US009090667B2

(12) United States Patent
Kim et al.

(10) Patent No.: US 9,090,667 B2
(45) Date of Patent: Jul. 28, 2015

(54) **CYCLIC PEPTIDE FROM *NONOMURAEA* SP., PROCESS FOR THE PRODUCTION THEREOF, AND PHARMACEUTICAL COMPOSITION FOR THE PREVENTION OR TREATMENT OF MYCOBACTERIA RELATED DISEASE COMPRISING THE SAME**

(75) Inventors: Jong Woo Kim, Gyeonggi-do (KR); Sang Wook Lee, Gyeonggi-do (KR); Sang Jin Park, Gyeonggi-do (KR); Joo Won Suh, Gyeonggi-do (KR); In Ae Lee, Gyeonggi-do (KR); Tae Mi Yoon, Gyeonggi-do (KR); Jong Keun Choi, Gyeonggi-do (KR); Ji Ean Lee, Gyeonggi-do (KR); Jin Yong Kim, Seoul (KR); Ying Yu Jin, Gyeonggi-do (KR); Scott Franzblau, Chicago, IL (US); Sanghyun Cho, Naperville, IL (US); Wei Gao, Chicago, IL (US); Guido Pauli, Darien, IL (US); James McAlpine, Green Oaks, IL (US); Jose Napolitano, Oak Park, IL (US); Birgit Jaki, Darien, IL (US); Brent Friesen, Oak Park, IL (US); Maria Florencia Rodriguez Brasco, Oak Park, IL (US); David Lankin, Schaumburg, IL (US)

(73) Assignees: Myongji University Industry and Academia Cooperation Foundation, Gyeonggi-do (KR); The Board of Trustees of the University of Illinois IL (US)

( * ) Notice: Subject to any disclaimer, the term of this patent is extended or adjusted under 35 U.S.C. 154(b) by 0 days.

(21) Appl. No.: 14/112,720

(22) PCT Filed: Apr. 18, 2012

(86) PCT No.: PCT/KR2012/002933
§ 371 (c)(1),
(2), (4) Date: Oct. 18, 2013

(87) PCT Pub. No.: WO2012/144790
PCT Pub. Date: Oct. 26, 2012

(65) Prior Publication Data

US 2014/0142031 A1 May 22, 2014

Related U.S. Application Data

(60) Provisional application No. 61/476,473, filed on Apr. 18, 2011, provisional application No. 61/513,403, filed on Jul. 29, 2011, provisional application No. 61/555,257, filed on Nov. 3, 2011, provisional application No. 61/607,934, filed on Mar. 7, 2012.

(51) Int. Cl.

| | |
|---|---|
| ***C07K 7/54*** | (2006.01) |
| ***C07K 7/08*** | (2006.01) |
| *A61K 38/00* | (2006.01) |

(52) U.S. Cl.
CPC ... *C07K 7/54* (2013.01); *C07K 7/08* (2013.01); *A61K 38/00* (2013.01)

(58) Field of Classification Search
None
See application file for complete search history.

(56) References Cited

U.S. PATENT DOCUMENTS

2010/0093615 A1 4/2010 Lamarche et al.

FOREIGN PATENT DOCUMENTS

WO WO 2009/119710 A1 10/2009

OTHER PUBLICATIONS

WHO Actions for Life—Towards a world free of tuberculosis; World Health Organization; Geneva, Switzerland, 2006.

WHO Anti-tuberculosis drug resistance in the world—Fourth Global Report, 2008.

Koenig, R., Drug-Resistant Tuberculosis, "In South Africa, XDR TB and HIV Prove a Deadly Combination", Science, Feb. 15, 2008, pp. 894-897, vol. 319.

World Health Organization, Global tuberculosis control: a short update to the 2009 report, Geneva, Switzerland: World Health Organization, 2009.

Kurt Hostettman et al., "The Search for New Drugs from Higher Plants", Chimia, 2007, pp. 322-326, vol. 61, No. 6.

Kurt Hostettman et al., "Plants as a Still Unexploited Source of New Drugs", Natural Product Communications, 2008, pp. 1307-1315, vol. 3, No. 8.

Kurt Hostettman et al., "Strategy in the search for new lead compounds and drugs from plants", Chimia 2005, pp. 291-294, vol. 59.

Torbjörn Lindblom, "Irreversible absorption of diphenylamine onto a straight phase and a reversed phase HPLC-column", Symposium on Chemical Problems Connected with the Stability of Explosives, Proceedings, 1993, $9^{th}$, 205-213.

Isao Kubo, "Recent applications of counter-current chromatography to the isolation of bioactive natural products", Journal of Chromatography, 1991, pp. 187-191, vol. 538.

(Continued)

*Primary Examiner* — Thomas S Heard
(74) *Attorney, Agent, or Firm* — Rabin & Berdo P.C.

(57) ABSTRACT

The present invention relates to novel anti-TB cyclic peptides from *Nonomuraea* sp. MJM5123, a process for the production of the anti-Tuberculosis peptide and a pharmaceutical composition for the prevention and treatment of mycobacterial infection comprising the same. The composition of the present invention is highly active against replicating/non-replicating *M. tuberculosis*, including MDR and XDR strains, so that it can be effectively used as a therapeutic agent for tuberculosis.

11 Claims, 10 Drawing Sheets

(56) References Cited

OTHER PUBLICATIONS

Paul C. Sadek et al., "A Radiochemical Study of Irreversible Adsorption of Proteins on Reversed-Phase Chromatographic Packing Materials", Analytical Biochemistry, 1986, pp. 359-371., vol. 153.
Julie D. Thompson et al., "The CLUSTAL_X windows interface: flexible strategies for multiple sequence alignment aided by quality analysis tools", Nucleic Acids Research, 1997, pp. 4876-4882, vol. 25, No. 24.
B. Becker et al., "Rapid Differentiation Between Nocardia and Streptomyces by Paper Chromatography of Whole-Cell Hydrolysates", Applied Microbiology, Sep. 1964, pp. 421-423, vol. 12, No. 5.
D.E. Minnikin et al., "An integrated procedure for the extraction of bacterial isoprenoid quinones and polar lipids", Journal of Microbiological Methods, 1984, pp. 233-241, vol. 2.
L Collins et al., "Microplate alamar blue assay versus BACTEC 460 system for high-throughput screening of compounds against *Mycobacterium tuberculosis* and *Mycobacterium avium*", Antimicrobial Agents and Chemotherapy, May 1997, pp. 1004-1009, vol. 41, No. 5.
Julian G. Hurdle et al., "A microbiological assessment of novel nitrofuranylamides as anti-tuberculosis agents", Journal of Antimicrobial Chemotherapy, 2008, pp. 1037-1045, vol. 62.
Ingrid Filliol et al., "Global Phylogeny of *Mycobacterium tuberculosis* Based on Single Nucleotide Polymorphism (SNP) Analysis: Insights into Tuberculosis Evolution, Phylogenetic Accuracy of Other DNA Fingerprinting Systems, and Recommendations for a Minimal Standard SNP Set, Journal of Bacteriology", Jan. 2006, pp. 759-772, vol. 188, No. 2.
Sebastien Gagneux et al., "Global phylogeography of *Mycobacterium tuberculosis* and implications for tuberculosis product development", Lancet Infect Dis, 2007, pp. 328-337, vol. 7, No. 5.
Sang Hyun Cho et al., "Low-Oxygen-Recovery Assay for High-Throughput Screening of Compounds against Nonreplicating *Mycobacterium tuberculosis*", Antimicrobial Agents and Chemotherapy, Apr. 2007, pp. 1380-1385, vol. 51, No. 4
Yuichi Terui et al., "New cyclic tetrapeptides from *Nonomuraea* sp. TA-0426 that inhibit glycine transporter type 1 (GlyT1)", Bioorganic & Medicinal Chemistry Letters, 2008, pp. 6321-6323, vol. 18.

*R*-β-OH-*L*-Phe N-Me-5-Methoxy-*L*-Trp N-Me-*L*-*allo*-Ile

CYCLIC PEPTIDE FROM *NONOMURAEA* SP., PROCESS FOR THE PRODUCTION THEREOF, AND PHARMACEUTICAL COMPOSITION FOR THE PREVENTION OR TREATMENT OF MYCOBACTERIA RELATED DISEASE COMPRISING THE SAME

The present application claims the benefit of U.S. Provisional Application No. 61/476,473, filed Apr. 18, 2011 and U.S. 61/513,403 filed Jul. 29, 2011 and U.S. 61/555,257 filed Nov. 3, 2011 and U.S. 61/607,934 filed Mar. 7, 2012, the contents of which are incorporated herein by reference.

TECHNICAL FIELD

The present invention relates to novel anti-mycobaterial peptides highly active against replicating/non-replicating *Mycobacterium tuberculosis* and various drug resistant *M. tuberculosis* strains including those that are multi-drug resistant (MDR) and extensively drug resistant Tuberculosis (XDR). The present invention also relates to a fermentation process of culturing strain of *Nonomuraea* sp. MJM5123 to prepare the antimycobacterial peptides and the process for production thereof and their pharmaceutical compositions comprising the anti-mycobacterial peptides of the present invention for the prevention and/or treatment of Tuberculosis.

BACKGROUND ART

*Mycobacterium tuberculosis* is a large, complex bacterium that causes tuberculosis (TB) disease in humans and other mammals. TB is a highly contagious disease that spreads from person to person by the respiratory route.

There were 9.4 million new TB cases in 2009, including 1.1 million cases among people with HIV and 0.3 million of MDR-TB [WHO *Actions For Life—Towards a world free of tuberculosis*; World Health Organization: Geneva, Switzerland, 2006]. MDR-TB requires the treatment duration to be extended from six months to at least two years. Worldwide prevalence of extensively drug resistant TB (XDR-TB) is estimated to be 6.6% among MDR *M. tuberculosis* strains [WHO *Actions For Life—Towards a world free of tuberculosis*; World Health Organization: Geneva, Switzerland, 2006].

Despite the keen awareness the epidemic has received, the prevalence of MDR—as well as XDR-TB continues to rise [WHO Anti-tuberculosis drug resistance in the world—Report #4. 2008]. The rapid emergence of MDR and XDR tuberculosis strains are difficult or virtually untreatable with current chemotherapies. Such strains pose a major global health threat, especially in developing countries and in countries with increasing prevalence of HIV/AIDS [Koenig, R. Drug-resistant tuberculosis. In South Africa, XDR TB and HIV prove a deadly combination. *Science* 2008, 319, 894-897].

The majority of people infected with latent TB infection (LTBI) are able to contain the bacilli from causing symptoms and pose no risk of infecting others. With the exception of obvious drug or disease-mediated immune suppression, little is known about what triggers LTBI to progress to active TB disease but once TB is able to circumvent immunological containment, it is considered to have progressed to active TB disease. Children and adults who are malnourished and/or immune-compromised are at increased risk of disease progression. In 2008, TB claimed the lives of 1.82 million people, of which 500,000 occurred among people infected with HIV, making it the leading cause of death for people with HIV [World Health Organization. Global tuberculosis control: a short update to the 2009 report. Geneva, Switzerland: World Health Organization, 2009].

Consequently, there is an urgent need for the development of new anti-TB drugs, preferably with a new mechanism of action.

DISCLOSURE OF INVENTION

Technical Problem

It is an object of the present invention to provide novel anti-TB peptides active against replicating/non-replicating *M. tuberculosis* and many drug resistant *M. tuberculosis* strains.

It is another object of the present invention to provide a process for the production of the anti-Tuberculosis peptides and a use of the anti-TB peptides in the pharmaceutical compositions for the prevention and/or treatment of various mycobacterial infections.

Solution to Problem

To achieve the above object, the present invention provides cyclic peptides isolated from a *Nonomuraea* sp. MJM5123 strain. In a preferred embodiment of the present invention, the cyclic peptide of the present invention can have the following Formula 1 or Formula 2:

[Formula 1: H-14]

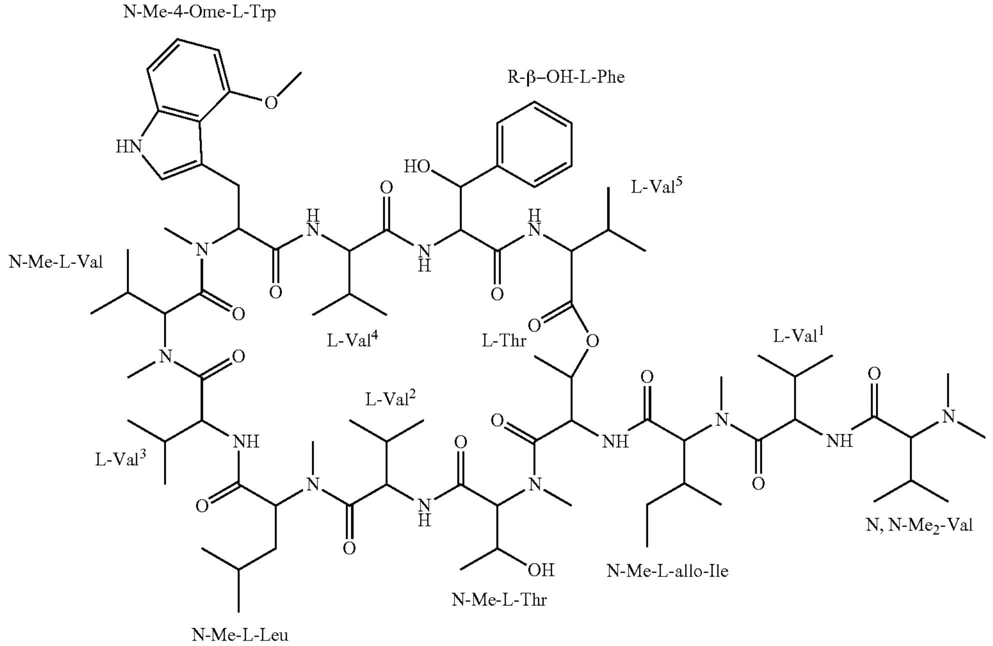

[Formula 2: H-16]

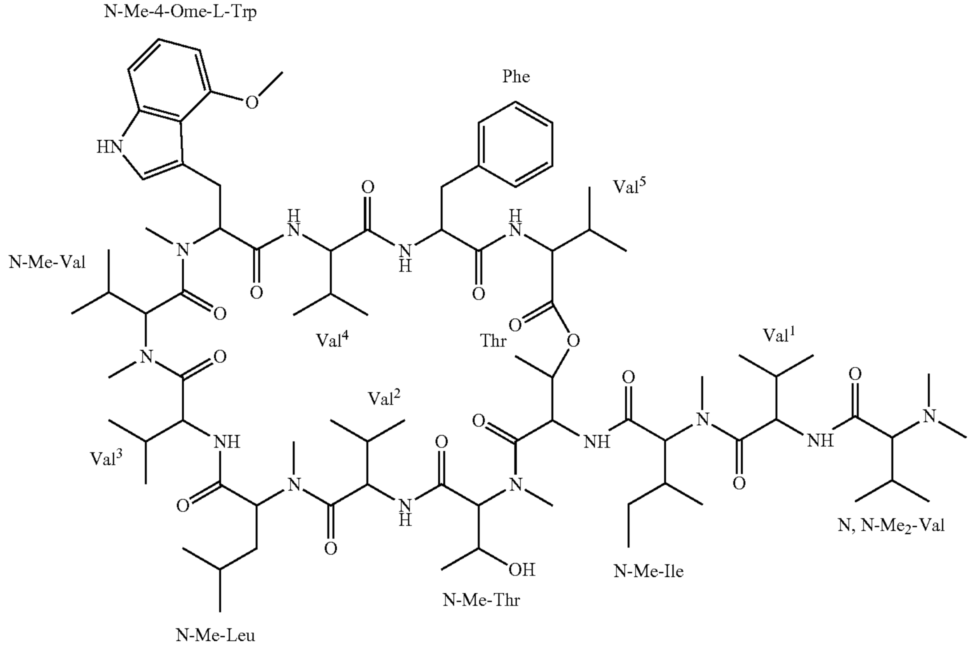

In addition, the present invention provides a pharmaceutical composition effective for the prevention and/or treatment of *Mycobacterium* spp. related diseases. In a preferred embodiment of the present invention, the pharmaceutical composition of the present invention comprises novel anti-TB cyclic peptides isolated from a *Nonomuraea* sp. MJM5123 strain and a pharmaceutically acceptable carrier for treating infections caused by Mycobacteria. The present inventors have deposited the *Nonomuraea* sp. MJM5123 at Korean Collection for Type Cultures (KCTC) of Korea Research Institute of Biotechnology and Bioscience (KRIBB) on Apr. 3, 2012 (Accession No: KCTC 12178BP).

Hereinafter, the present invention is described in detail.

The present invention provides cyclic peptides isolated from a *Mycobacterium* spp., preferably a *Nonomuraea* sp. MJM5123 strain. In a preferred embodiment of the present invention, the cyclic peptide of the present invention has the Formula 1 or Formula 2. Preferably, the cyclic peptides of the present invention can be isolated from a *Nonomuraea* sp. MJM5123 strain through the following procedures:

Actinomycetes—a Source for New Anti-TB Antibiotics

Actinomycetes are ubiquitous soil organisms known to produce a great variety of secondary metabolites. Several antibiotics, used for the treatment of a variety of bacterial infections, originate from actinomycetes including streptomycin, cephalosporins, tetracycline, erythromycin, rifampin, and daptomycin. Although three different drugs used today to treat tuberculosis (rifampin, streptomycin, and cycloserine) were discovered from actinomycetes by using agar diffusion assays, these screens were not initially conducted using *M. tuberculosis*. This was due to the contagious nature and often fatal outcome (at the time) of TB. Because we now understand that *M. tuberculosis* is uniquely susceptible to several classes of antimicrobial agents, we must assume that the past failure to screen fermentation broths directly against this pathogen resulted in many potentially useful compound classes going undetected. We therefore initiated this TB drug discovery program by screening directly against a virulent strain of *M. tuberculosis.*

High-Throughput Screening

Techniques for the high throughput screening of either pure compounds or extracts were established at the Institute for Tuberculosis Research (ITR). The Extract Collection of Useful Microorganisms (ECUM) at Myongji University in South Korea maintains a culture collection of over 7000 actinomycete isolates from Korea, China, Nepal, Philippines, Vietnam, Antarctica, and the Arctic Circle. The inclusion of rather exotic locations was an attempt at isolating rare and novel species.

Each isolate was initially fermented in 20 ml cultures in 3 different culture media—G.S.S. (rich medium), Bennett's and GYC (minimal medium) and three extracts per strain were tested in the Microplate Alamar Blue Assay (MABA) and further prioritized.

Identification of MJM5123

After screening over 65,000 extracts stored in The Extract Collection of Useful Microorganisms (ECUM) at Myongji University in Korea, the methanol extract of mycelium from a novel actinomycetes species, strain MJM5123 was found to have a strong anti-TB activity. Strain MJM5123 was identified as a *Nonomuraea* sp. by a polyphasic taxonomic approach.

Bioassay-Guided Isolation

Strain MJM5123 was selected for a bioassay-guided isolation procedure based on an initial fractionation with vacuum-liquid chromatography (VLC) followed by a targeted purification with several high-speed counter current chromatography (CCC) steps.

The bioassay-guided search for bioactive principles of natural products requires preparative analytical techniques that are capable of resolving complex mixtures efficiently [Hostettmann, K.; Marston, A. The search for new drugs from higher plants. *Chimia* 2007, 61, 322-326; Hostettmann, K.; Marston, A. Plants as a still unexploited source of new drugs. *Nat Prod Com* 2008, 3, 1307-1315; Hostettmann, K.; Marston, A.; Wolfender, J.-L. Strategy in the search for new lead compounds and drugs from plants. *Chimia* 2005, 59, 291-294]. The contemporary standard methods in this area are various forms of solid-liquid chromatography that utilize solid stationary phases, such as in column/flash, vacuum, and high-performance liquid chromatography (CC, VLC, HPLC). However, there are several shortcomings associated with the use of solid stationary phases (adsorbents), which significantly limit their function in the context of bioassay-guided fractionation: Irreversible adsorption is one of these limitations and widely recognized [Lindblom, T. Irreversible absorption of diphenylamine onto a straight phase and a reverse phase HPLC-column. *Symposium on Chemical Problems Connected with the Stability of Explosives, [Proceedings]* 1993, 9th, 205-213; Kubo, I. Recent applications of counter-current chromatography to the isolation of bioactive natural products. *J Chrom* 1991, 538, 187-191; Sadek, P. C.; Carr, P. W.; Bowers, L. D.; Haddad, L. C. A radiochemical study of irreversible adsorption of proteins on reversed-phase chromatographic packing materials. *Anal Biochem* 1986, 153, 359-371]. Accordingly, LC methods are frequently associated with the loss of material (limited recovery) and, more importantly, the attenuation of the bioactivity along the fractionation pathway. These limitations do not exist in countercurrent chromatography (CCC), because as a liquid-liquid technique, which entirely relies on the partition of a sample between two immiscible solvents to achieve separation, it allows the full recovery of the sample material and hence gives the potential to assess synergetic effects of complex natural product mixtures. Moreover it is an ideal method for a targeted isolation of specific compound classes. Thus, our isolation procedure is mainly based on CCC.

Strain MJM5123 was mass cultured in 20 L fermentors at ECUM, harvested and extracted in order to produce sufficient biomass for isolation, structure elucidation and biological profiling of the pure compounds H-14 and H-16, two highly anti-TB active cyclic peptides.

Structure Elucidation of Bioactive Constituents

Full structure elucidation of H-14 and H-16 was performed utilizing the highest quality and state-of-the-art 1D/2D NMR- and high resolution MS-based structural information, augmented by X-ray crystallography of the peptide. Quantitative NMR (qNMR) was used for the simultaneous selective recognition and quantitative determination of every isolation step. QNMR is an optimal tool not only for determination of purity and/or quantity of active isolates but also for the purpose of profiling biologically active but still complex compounds mixtures/fractions. The overall 3D structure of H-14 and its amino acid residues were determined by X-ray crystallography.

Optimization of Fermentation Process

For improving productivity of anti-TB peptides, an optimal fermentation process and cost-effective media were developed. The main fermentation was performed at 34° C. with an agitation speed of 600 rpm and 0.3 vvm of aeration for 6 days. The final packed mycelium volume was 80% at pH 8.20 and total sugar was less than 1.8%. The fermentation process yielded 373 mg/L of H-14.

In addition, the present invention provides a pharmaceutical composition effective for the prevention and/or treatment of *Mycobacterium* spp. related disease comprising a compound of Formula 1 and/or Formula 2 of the present invention as an active ingredient. In a preferred embodiment, the *Mycobacterium* spp. related disease is tuberculosis. In another preferred embodiment of the present invention, the tuberculosis can be a MDR tuberculosis or XDR tuberculosis.

The pharmaceutical composition of the present invention comprises the novel anti-TB peptides of the present invention isolated from a *Nonomuraea* sp. MJM5123 stain. Preferably, the pharmaceutical composition of the present invention may further comprise a pharmaceutically acceptable carrier, an excipient and a diluent.

In one embodiment of the present invention, the cyclic peptides of the present invention can be treated alone as a therapeutic agent for Tuberculosis, or can be treated in combination with a mixed composition of one or at least two kinds of other anti-mycobacterial agent. In a preferred embodiment of the present invention, the anti-mycobacterial agent can be a 1st line oral antituberculosis agents, such as isoniazid, rifampicin, ethambutol and pyrazinamide; a injectable anti-TB agent such as streptomycin, amikacin, capreomycin and kanamycin; a fluoroquinolone such as ciprofloxacin, ofloxacin and moxifloxacin; a 2nd line oral anti-TB agent such as rifabutin, protionamide, ethionamide, cycloserine, PAS and thioacetazone; other anti-TB agents such as linezolid, clofazimine, amoxicillin/clavulanate, and a derivative of diaminodiphenylsulphone; and a compound currently in clinical trials for tuberculosis such as Bedaquiline, PA-824, Dalamanid, SQ-109, Sutezolid, rifapentine and compounds in pre-clinical development, in particular AZD5847, BTZ043, TBA-354, CPZEN-45, SQ-641, SQ-609, DC-159a, Q201, THPP, riminophenazine analogs of clofazimine and boron-containing LeuRS inhibitors, but not always limited thereto.

The anti-TB cyclic peptides of the present invention can be formulated for oral administration, for example powders, granules, tablets, pills, capsules, solutions, suspensions, emulsions, and syrups. The carriers, excipients and diluents are exemplified by lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil.

Solid formulations for oral administration are tablets, pills, powders, granules and capsules. These solid formulations are prepared by mixing with one or more suitable excipients such as starch, calcium carbonate, sucrose or lactose, gelatin, etc. Except for the simple excipients, lubricants, for example magnesium stearate, talc, etc, can be used.

Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Novel anti-TB peptides of the present invention can be formulated for intravenous injection. For intravenous (IV) use, a water soluble form of a compound of the present invention can be dissolved in any of the commonly used intravenous fluids and administered by infusion. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Anti-TB peptides of the present invention also may be placed in injectors, cannulae, catheters and lines.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. Novel anti-TB peptides of the present invention can be dissolved in polyethylene glycol, propylene glycol, ethanol, corn oil, benzyl alcohol, sodium chloride, and/or various buffers.

For intramuscular, parenteral or intravenous preparations, a sterile formulation of anti-TB peptides or a suitable soluble salt form of the compound, for example the hydrochloride salt, can be dissolved and administered in a pharmaceutical diluent such as Water-for-Injection (WFI), physiological saline or 5% glucose.

A suitable insoluble form of the anti-Tuberculosis peptides also may be prepared and administered as a suspension in an aqueous base or a pharmaceutically acceptable oil base, e.g., an ester of a long chain fatty acid such as ethyl oleate. Injectable depot forms may be made by forming microencapsulated matrices of the anti-TB peptides in biodegradable polymers such as polylactide-polyglycolide. Depending upon the ratio of drug to polymer and the nature of the particular polymer employed, the rate of drug release can be controlled. Biodegradable polymers include poly-orthoesters and poly-anhydrides. Depot injectable formulations are also prepared by entrapping the drug in microemulsions that are compatible with body tissues.

For application to the eyes or ears, the peptides of the present invention can be formulated in hydrophobic or hydrophilic bases as ointments, creams, lotions, paints or powders.

For application to rectal administration, the peptides of the present invention can be formulated in the form of suppositories admixed with conventional carriers such as cocoa butter, wax or other glyceride.

The anti-TB peptides of the present invention also may be used in inhalers, such as metered dose inhalers, and nebulizers.

The present invention further provides a process for the manufacture of the anti-Tuberculosis cyclic peptide of the Formula or Formula 2 of the present invention. The process of the present invention can comprises the following steps: cultivating an antimycobacterial peptide-producing microorganism of the *Nonomuraea* sp. MJM5123 strain under aerobic conditions in an aqueous culture medium; and isolating anti-Tuberculosis cyclic peptides of the present invention from fermented mycelia.

In one embodiment of the present invention, the step for isolating anti-Tuberculosis cyclic peptide can comprise the following steps: performing Vacuum liquid chromatography (VLC) of methanol extract of *Nonomuraea* sp. MJM5123 mycelia using methanol and chloroform as an eluent; performing Sephadex LH-20 open column chromatography using methanol as an eluent; and performing High Speed Countercurrent Chromatography (HSCCC) using HEMWat+2 as an solvent.

In another embodiment of the present invention, the step for isolating anti-Tuberculosis cyclic peptide can comprise the following steps: extracting *Nonomuraea* sp. MJM5123 mycelia using methanol as a solvent; adding water up to 30% of the methanol extract to make aqueous methanol; defatting the methanol extract using hexane; separating aqueous layer and adjusting to 65% aqueous methanol; extracting the aqueous layer using chloroform; concentrating and resolving the chloroform extract using methanol; performing Sephadex LH-20 column Chromatography using methanol as an eluent; and performing HPLC equipped with column filled with reverse phase gel (RP-18).

Advantageous Effects of Invention

Novel anti-TB cyclic peptides have very low cyto-toxicity against mammalian cells and potent activity against replicating/non-replicating *M. tuberculosis* including single drug resistant *M. tuberculosis* strains, MDR and XDR-TB, so that they can be effectively used as therapeutic agents for tuberculosis.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Microbial Extract Libraries for High-Throughput Screening

Figure 1:
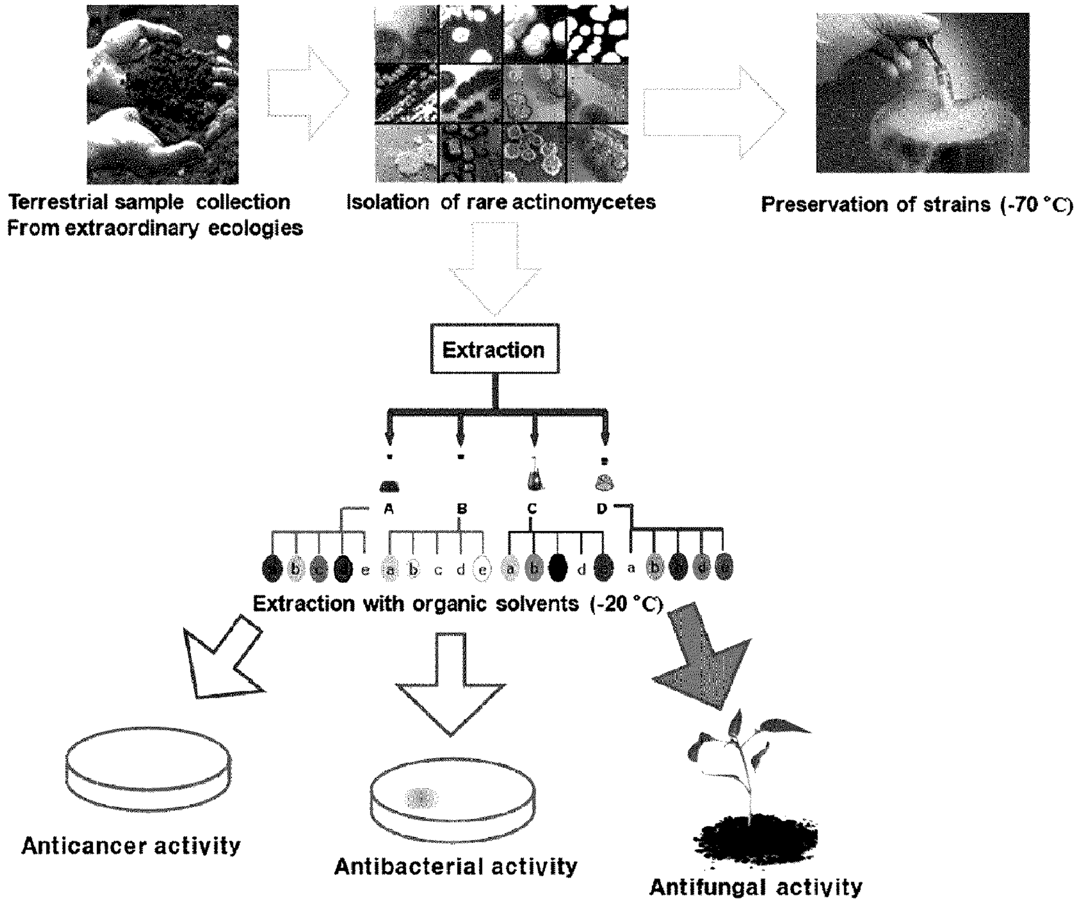
FIG. 1 shows the process for establishment of microbial extract libraries.
Figure 2:
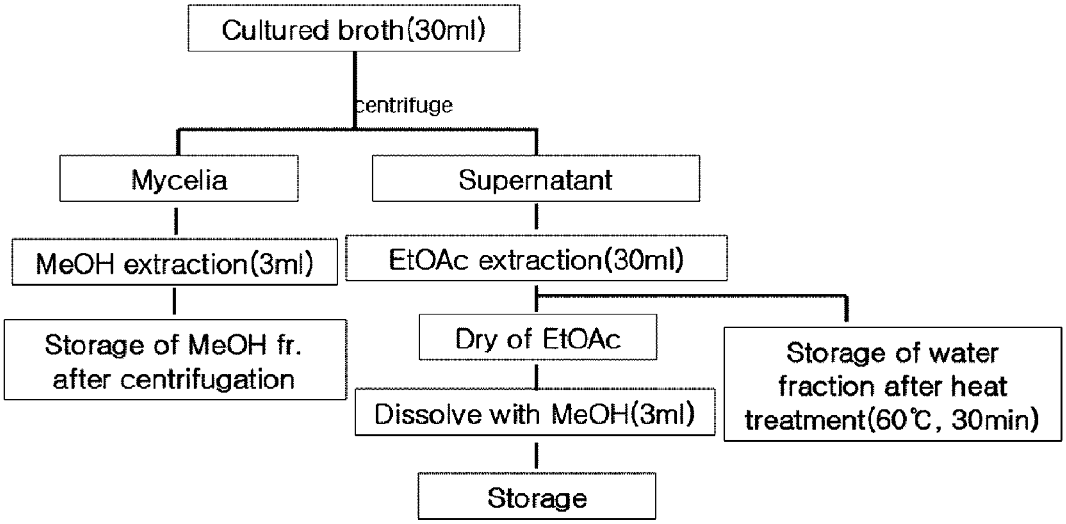
FIG. 2 shows a overview of extraction process of the present peptides.

Approximately 7,000 actinomycetes isolates were isolated from soil samples collected in areas with unique weather conditions and ecologies such as alpine regions, tropical regions, polar regions, deserts, volcano and so on, and have been maintained by The Extract Collection of Useful Microorganisms (ECUM) at Myongji University in Korea. Nine different kinds of extracts were prepared from each isolate for screening anti-TB candidates. First, each isolate was cultured with 30 ml of G.S.S, Bennett's, and GYC. After mycelium and culture broth were separated by centrifugation, the mycelium was extracted with methanol and the culture supernatant was partitioned with ethyl acetate and water respectively. Finally, nine organic and aqueous extracts from each microbial isolate cultured in three media were concentrated to dryness by vacuum evaporator and preserved in a deep freezer at −70° C. (FIG. 1, FIG. 2 and Table 1).

TABLE 1

| Three major media for Actinomycetes |
|---|
| <1> G.S.S. medium |
| Soluble starch 10 g |
| Glucose 20 g |
| Soybean meal 25 g |
| Beef extract 1 g |
| Yeast extract 4 g |
| NaCl 2 g |
| $K_2HPO_4$ 0.25 g |
| $CaCO_3$ 2 g |
| D.W. 1 L |
| pH 7.2 |
| <2> Bennett's medium |
| Glucose 10 g |
| Yeast extract 1 g |
| Bacto-peptone 2 g |
| Beef extract 1 g |
| <3> DYC medium |
| Dextrine 25 g |
| Dry yeast 12 g |
| CSL 20 g |
| NaBr 1 g |
| $CoCl_2$ 1 g |
| pH 7.0 |
| D.W. 1 L |

Example 2

Large-Scale Screening

Each actinomycete isolate of ECUM was initially fermented in 20 ml cultures in three different culture media—G.S.S. (rich medium), Bennett's and GYC (minimal medium). The mycelium was extracted with methanol and the culture supernatant with ethyl acetate which was subsequently partitioned with water producing nine extracts per isolate. Aliquots of 100 μl were dried and shipped from Myongji University to UIC in 96-well plates, solubilized in 100 μl DMSO and diluted 1:100 into test cultures. HTS of ~63,000 extracts, yielded 349 extracts (0.55%) with=90% inhibition of *M. tuberculosis* in 7H12 medium (palmitic acid as C source) as determined by fluorometric readings in the Microplate Alamar Blue Assay (MABA). Ninety of the initial hits were then re-fermented at a one liter scale at ECUM and the extracts subsequently fractionated at UIC with solid phase reversed-silica gel extraction with a MeOH-water gradient 20-100% followed by $CHCl_3$ 100% to yield six fractions per extract. Fractions were biologically profiled in terms of: 1.) mammalian cell toxicity (VERO cells $IC_{50}$); 2.) activity against non-replicating *M. tuberculosis* (LORA); 3.) activity against *M. tuberculosis* strains resistant to rifampin (RMP), isoniazid (INH), streptomycin (SM), kanamycin (KM), capreomycin (CAP), cycloserine (CS), (to be sure that we are not merely finding these actinomycete-derived antibiotics again) or moxifloxacin (Mox) and 4.) activity against *M. smegmatis, S. aureus, E. coli* and *C. albicans*. Based on these results, 20 actinomycete strains were prioritized for further investigation.

Example 3

Identification of MJM5123

Determination of Morphological and Cultural Characteristics

Figure 3:
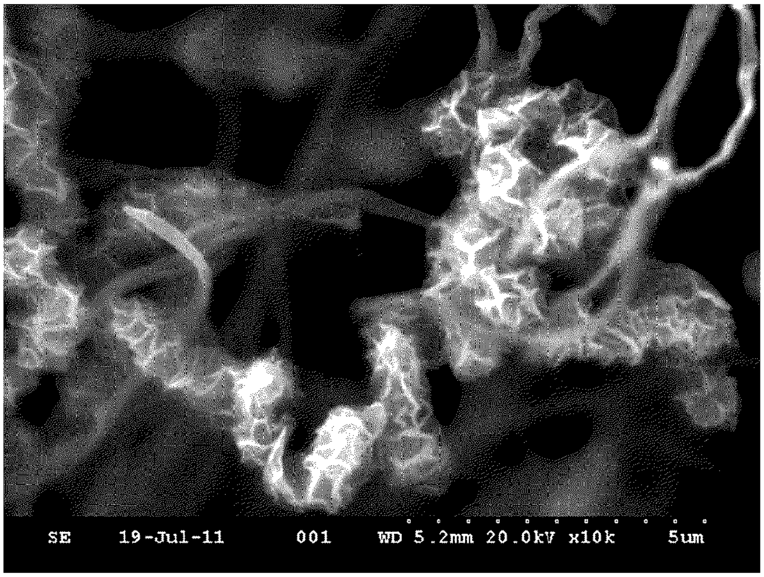
FIG. 3 shows a scanning electron micrograph of *Nonomuraea* sp. MJM5123 grown on ISP3 medium for 2 weeks at 28° C.

MJM5123 was isolated from a soil sample collected on Mount Halla, Korea. The genus of the strain was identified by characteristic morphology and chemical analysis of cell wall components. To determine morphological and cultural characteristics, the strain was grown for 2 weeks at 28° C. on the International Streptomyces Project (ISP) media (Shirling, E. B. and D. Gottlieb, Methods for characterization of Streptomyces species. Int J Syst Evol Microbiol. 1966 16 (Pt 3): 313-330) such as yeast extract malt extract agar (ISP2), oatmeal agar (ISP3), inorganic salts starch agar (ISP4), glycerol asparagine agar (ISP5). The colony colors were determined by using the Color Harmony Manual (Jacobson, E., W. C. Grauville, et al., Color Harmony Manual. 1958. Chicago, Container Corporation of America). The spores and mycelia were observed by scanning electron microscopy (Hitachi, S-3500N, Japan) (FIG. 3).

TABLE 2

Cultural characteristics of MJM5123

| Agar medium | *Nonomuraea* sp. MJM5123 Growth/reverse color/ aerial mycelium/sporulation |
|---|---|
| Yeast-malt extract (ISP2) | ++/beige/−/− |
| Oatmeal (ISP3) | +/beige/++/++ |
| Salts-starch (ISP4) | +/beige/−/− |
| ISP5 | +/beige/−/− |
| ISP6 | +/beige/−/− |
| Tyrosine (ISP7) | +/beige/−/− |

Growth and sporulation on aerial mycelium are scored as:
++, good;
+, moderate;
±, poor;
−, no growth and no spore formed The strain grew well on ISP2 medium and showed moderate growth on the other media. The color of vegetative mycelium and aerial mycelium was beige without diffusible pigment. White spores were formed only on oatmeal medium (ISP3) and the scanning electron micrograph revealed spiral chains of rugose spores on aerial mycelia.

To test for melanoid pigments, peptone yeast extract iron agar (ISP6) and tyrosine agar (ISP7, with or without tyrosine) was used. Temperature range, NaCl tolerance and pH range for growth was determined on ISP3 medium and antibiotic resistance test was performed on ISP2 medium for 2 weeks at 28° C.

TABLE 3

Physiological characteristics of *Nonomuraea* sp. MJM5123

| Growth at NaCl (%) | |
|---|---|
| 0 | ++ |
| 1 | ++ |
| 2 | + |
| 3 | ++ |
| 4 | − |
| **Growth at temperature (° C.)** | |
| 15 | − |
| 20 | + |
| 25 | + |
| 28 | ++ |
| 37 | ++ |
| 45 | − |
| **Growth at pH** | |
| 5 | ++ |
| 6 | ++ |
| 6.8 | ++ |
| 7.2 | ++ |
| 9 | ++ |
| **Melanin pigment** | |
| With tyrosine | − |
| Without tyrosine | − |

Characteristics are scored as
(++), positive;
(+), moderate;
(−), negative

MJM5123 assimilated tyrosine as a nutrient source without producing melanin, and the strain was able to grow at pH 5.0~9.0 and 0~3.0% of NaCl and showed good growth at 20° C.~37° C. MJM5123 was susceptible to apramycin, kanamycin, vancomycin and thiostrepton but resistant to ampicillin.

TABLE 4

| Growth in the presence of antibiotics (50 μg/ml) Antibiotic resistance (μg/ml) | |
|---|---|
| Apramycin (50) | − |
| Kanamycin (50) | − |
| Ampicillin (50) | + |
| Vancomycin (50) | − |
| Thiostrepton (50) | − |

Characteristics are scored as
(+), positive;
(−), negative

ISP9 agar medium was used as a basal medium to examine utilization of carbohydrates as sole carbon sources. Stock solutions (10% w/v) of carbohydrates (Sigma Aldrich, CAR10) were sterilized by filtration and added to autoclaved ISP9 medium at a final concentration of 1.0%. MJM5123 utilized hexoses, pentose, alcohol sugars and disaccharide (Table 5).

TABLE 5

Carbohydrate utilization

| Utilization of: | MJM5123 |
|---|---|
| Glucose | ++ |
| Arabinose | ++ |
| Sucrose | ++ |
| Xylose | ++ |
| Inositol | + |
| Mannitol | ++ |
| Fructose | ++ |
| Rhamnose | ++ |
| Raffinose | + |

Characteristics are scored as
(++), positive;
(+), moderate;
(−), negative

Determination of Chemotaxonomic Characters

For chemotaxonomic characterization of the cell wall components, freeze-dried mycelium were prepared by growing in trypticase soy broth (TSB) on a rotary shaker for 7 days at 28°

C. The stereoisomers of diaminopimelic acid (DAP) and glycine were determined by TLC [Becker, B.; Lechevalier, M. P.; Gordon, R. E.; Lechevalier, H. A. Rapid differentiation between Nocardia and Streptomyces by paper chromatography of whole-cell hydrolysates. *Appl Microbiol* 1964, 12, 421-423]. 5 mg of dry cells was sealed in a small ampoule together with 1 ml of 6N hydrochloric acid. The ampoule was stored overnight at 100° C. in an oven. The air-cooled hydrolysate was filtered through Whatman no. 1 filter paper. The filtrate was concentrated to dryness and dissolved in 0.3 ml of distilled water. 2 μl of the solution was spotted on a TLC plate (Merck, TLC Cellulose F glass plate no. 105718) and developed with the solvent system methanol:distilled water: 6N HCl:pyridine (80:26:4:10, vol/vol) for 4 hours. After air drying, 0.2% ninhydrin solution (in acetone) was sprayed and heated at 100° C. for 3 min to reveal the spots. 1 μl of 0.1M D, L-DAP (Sigma Aldrich, No. D-1377) and 1 μl of 0.1M glycine (Sigma Aldrich, No. 50046) were used as authentic standards. Glycine and D, L-DAP spots were visualized as gray-green.

Figure 4:
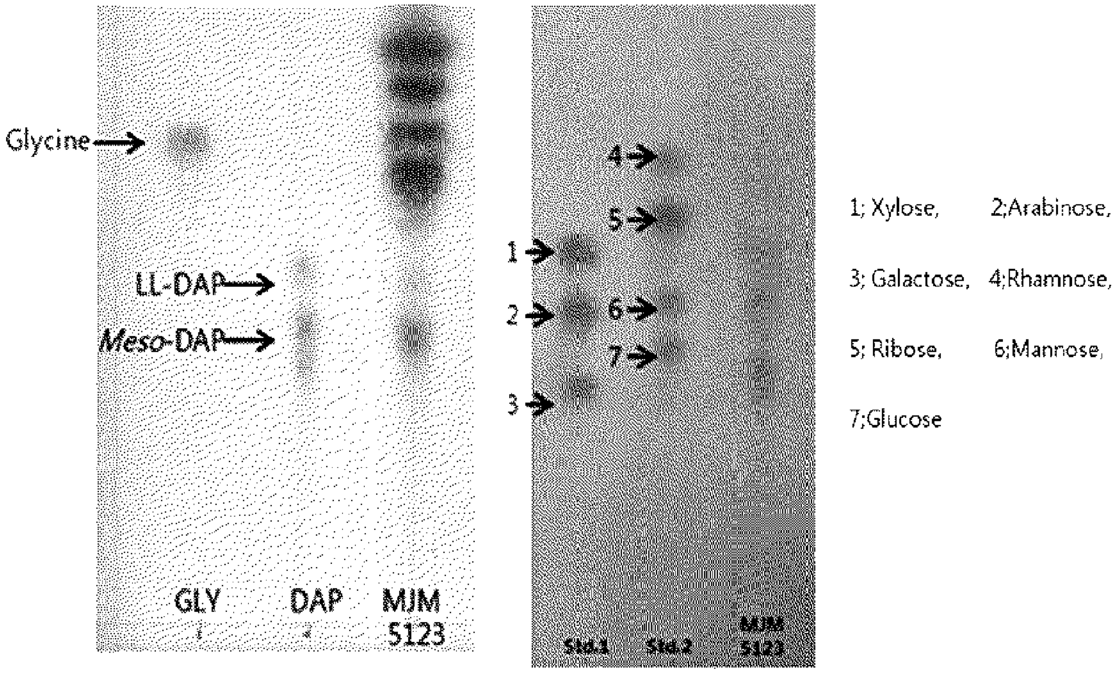
FIG. 4 shows the result of whole cell hydrolysates analysis of *Nonomuraea* sp. MJM5123.

Saccharide analysis was carried out with a slightly modified method of Lechevalier. 50 mg of dry cells was boiled for 2 hours in a sealed ampoule with 2.0 ml of 1N sulfuric acid. The cooled hydrolysate was transferred to a 50 ml conical centrifuge tube and pH was adjusted to 5.4 by saturated barium hydroxide. After centrifugation, the supernatant was concentrated to 0.3 ml and non-resolved particles were removed by centrifugation. 1 μl of the solution was loaded on a TLC plate (Merck, TLC Cellulose F glass plate no. 105718). The first saccharides (Sigma Aldrich, car10) standard containing xylose, arabinose, galactose, and the second (Sigma Aldrich, CAR10) containing rhamnose, ribose, mannose, glucose were applied each at 1% concentration with the solvent system n-butanol:distilled water:pyridine:toluene (10:6:6:1, vol/vol) for 4 hours. After spraying aniline phthalate solution (3.25 g of aniline hydrogen phthalate (TCI-GR, No. P0284), dissolved in 100 ml of water saturated butanol) the TLC plate was heated at 100° C. for 4 min. Glycine and D, L-DAP were constituents of the peptidoglycan of MJM5123 and the major sugars were xylose, galactose, mannose, glucose in the whole cell hydrolysates (FIG. 4).

Polar lipids and menaquinones were extracted by the method of Minnikin et al. [Minnikin, D. E.; O'Donnella, A. G.; Goodfellowb, M.; Aldersonb, G.; Athalyeb, M.; Schaala, A.; Parlett, J. H. An integrated procedure for the extraction of bacterial isoprenoid quinones and polar lipids. J Microbiol Methods 1984, 2, 233-241]. 2 ml of methanol:distilled water (100:10, vol/vol) and 2 ml of petroleum ether were added to 50 mg of dry cell and mixed for 15 min. The upper layer was transferred to a new vial. 1 ml of petroleum ether was added to the lower layer and mixed. The combined upper layers were evaporated under nitrogen gas at room temperature and the residue was used for the analysis of menaquinones. The polar lipids were extracted from the lower layer. The lower layer was heated in a boiling water bath for 5 min. After cooled at 37° C., 2.3 ml of chloroform:methanol:water (90:100:30, vol/vol) solution was added and mixed for 60 min. Following centrifugation the supernatant was transferred to a new tube. The lower layer was extracted by mixing with 0.75 ml of chloroform:methanol:water (50:100:40, vol/vol) solution for 5 min and the separated supernatant was combined with the above tube. This step was repeated once more. The collected supernatant was thoroughly mixed with 1.3 ml of chloroform and 1.3 ml of 0.3% sodium chloride solution. After partitioning by centrifugation, the upper layer was discarded and lower layer was dried under nitrogen gas at room temperature. The polar lipid extract was dissolved in 60 μl of chloroform:methanol (2:1, vol/vol), and 10 μl of solution was spotted on a TLC plate (Merck, TLC Silica gel 60 F254 glass plate no. 105729) and identified by a two-dimensional TLC method using chloroform:methanol:distilled water (65:25:4, vol/vol) and was chloroform:acetic acid:methanol:distilled water (40:7.5:6:2, vol/vol) as developing solvents. The polar lipids were visualized by spraying with four reagents, 5% phosphomolybdic acid solution in ethanol (Sigma Aldrich, P4869), 0.2% ninhydrin solution in water-saturated n-butanol (Sigma Aldrich, N4876), α-naphthol sulfuric acid and molybdenum blue (Sigma Aldrich, M1942).

Figure 5:
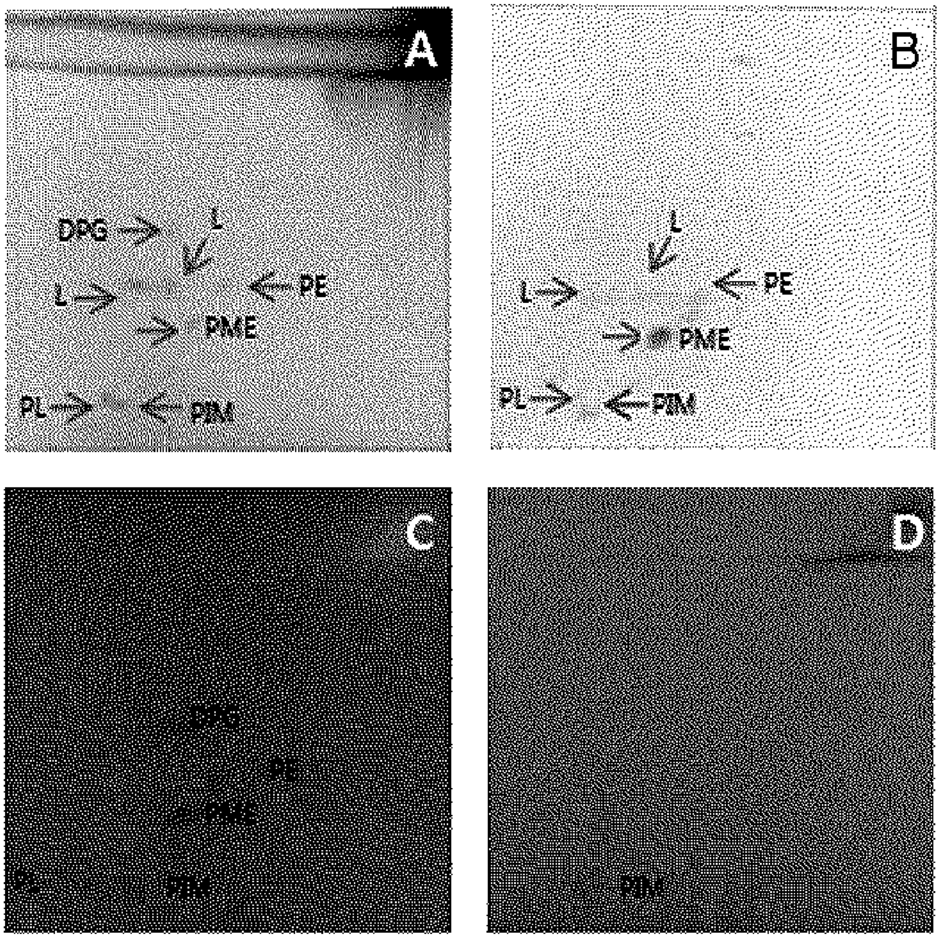
FIG. 5 shows a polar lipid profile of *Nonomuraea* sp. MJM5123. Plates were sprayed with molybdatophosphoric acid to detect total lipids (a), ninhydrin to detect aminolipids (b), molybdenum blue to detect phospholipids (c), and α-naphtholsulfuric acid to detect glucolipids (d).

Polar lipid analysis revealed that the polar lipid of MJM5123 comprised of phosphatidylethanolamine (PE), diphosphatidylglycerol (DPG), phosphatidylmonomethylethanolamine (PME), phosphatidylinositol mannoside (PIM), unknown phospholipid (PL) and an unknown polar lipid (L) (FIG. 5).

The cellular fatty acids were analyzed by using the Microbial Identification System (MIDI, version 4.5) combined with gas chromatography and identified with the ACTIN6 database. The major cellular fatty acid was iso-C16:0 (25.5%); various other fatty acids were also detected (Table 6).

TABLE 6

The fatty acid composition of MJM5123

| Fatty acid | MJM 5123(%) |
|---|---|
| 16:0 ISO | 25.5 |
| 17:1 CIS 9 | 10.5 |
| 15:00 | 10.1 |
| 16:00 | 9.6 |
| 15:0 ISO | 9.3 |
| 16:1 CIS 9 | 4.3 |
| 17:0 10METHYL | 3.9 |
| 17:00 | 3.0 |
| 16:0 ISO 2OH | 2.9 |
| 16:1 ISO G | 2.6 |
| 14:00 | 2.4 |
| 14:0 ISO | 2.2 |
| 16:0 10METHL | 1.6 |
| 17:0 ANTEISO | 1.6 |
| 17:0 ISO | 1.4 |
| 15:0 ANTEISO | 1.2 |

Values are percentages of total cellular fatty acids. Trace amounts less than 1.0% are not shown Phylogenetic Analysis The 16S rDNA was amplified from the MJM5123 genomic DNA with a primer pair of 27f (5'-AGAGTTTGATCCTGGCTCAG-3', SEQ. ID. NO: 1) and 1492r (5'-GGTTACCTTGTTACGACTT-3', SEQ. ID. NO: 2). The amplified DNA was sequenced using the same primers as above on an ABI 3730XL capillary DNA Sequencer (Applied Biosystems, USA). The computer-aided comparison of the 16S rDNA was carried out using the NCBI BLAST available at http://www.ncbi-nlm-nih.gov/.

A phylogenetic tree was constructed by a neighbor-joining method using MEGA4.0 software. Branch support for the phylogenic tree was generated by 1,000 bootstrap replications.

According to a BLAST search, the 16S rDNA sequence showed 98% similarity with *Nonomuraea rubra* DSM 43768T, *Nonomuraea roseola* DSM 43767T and 97% similarity with *Nonomuraea dietziae* DSM 44320T. The phylogenetic analysis revealed that MJM5123 belonged to the *Nonomuraea* family, but is located on a different subclade from the closely related strains.

Figure 6:
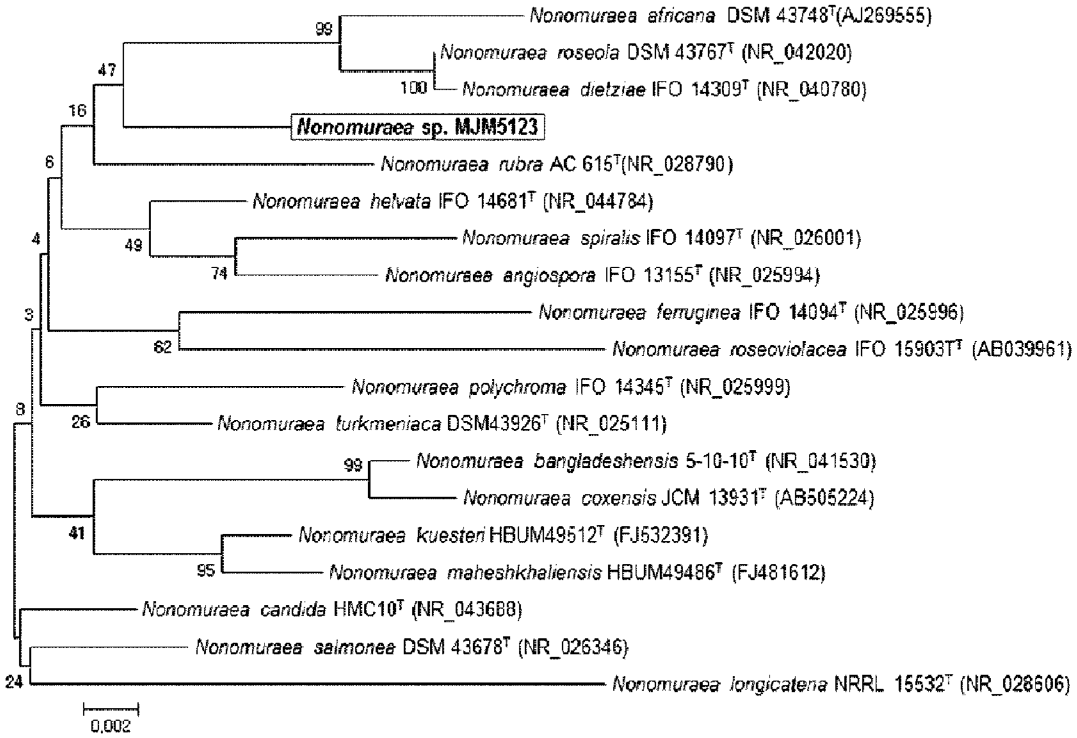
FIG. 6 shows a phylogenic analysis, based on 16S rDNA sequences available from the NCBI database, constructed after multiple alignment of data by CLUSTAL-X [Thompson, J. D.; Gibson, T. J.; Plewniak, F.; Jeanmougin, F.; Higgins, D. G. The CLUSTAL_X windows interface: flexible strategies for multiple sequence alignment aided by quality analysis tools. *Nucleic Acids Res* 1997, 25, 4876-4882].

Distances were obtained (using distance options according to the Kimura-2 model) and clustering was performed, using the neighbor-joining method, by using the software package MEGA, version 4.0. Bootstrap values based on 1000 replications are listed as percentages at the branching point. Bar indicates 0.002 substitutions per nucleotide (FIG. 6).

DNA Relatedness with Closely Related Strain

The DNA-DNA relatedness with closely related strains was evaluated by fluorometric analysis using the microplate hybridization method. The DNA-DNA relatedness values were 34%~65% indicating that MJM5123 represented a separate genomic species (Table 7).

TABLE 7

DNA-DNA hybridization

| Taxa | MJM5123 (%) |
|---|---|
| MJM5123 | 100 |
| *N. dietziae* DSM 44320$^T$ | 65 |
| *N. roseola* DSM 43767$^T$ | 65 |
| *N. rubra* DSM 43768$^T$ | 34 |

The present inventors have deposited the *Nonomuraea* sp. MJM5123 at Korean Collection for Type Cultures (KCTC) of Korea Research Institute of Biotechnology and Bioscience (KRIBB) on Apr. 3, 2012 (Accession No: KCTC 12178BP).

Example 4

Optimization of Fermentation Process

For improving productivity of anti-TB peptides, an optimal fermentation process and cost-effective media were developed. The strain MJM5123 can utilize a variety of carbon and nitrogen sources such as glucose, fructose, maltose, galactose, xylose, sucrose, glycerol, soybean oil, starch, dextrin, amino acids, yeast extract, pancreatic digested casein, beef extract, peptone, malt extract, oatmeal, soybean meal, enzymatic digested soybean meal, cotton seed meal, corn steep liquid, inorganic salts and the like. MJM5123 grew at a wide range of temperatures and pH (between 20° C. and 40° C., pH 5.0~9.0). It is however advantageous to adjust the initial medium pH to ~7.2 before inoculation. The most efficient growth and titer was achieved when the fermentation temperature was maintained at 34° C. A three-stage fermentation procedure and media for each stage were developed for cost-effective production and ease of downstream processing, as follows;

TABLE 8

Activation medium (AM)

| Ingredient | Amount (%) |
|---|---|
| Soluble starch | 2.000 |
| Yeast extract | 0.500 |
| Beef extract | 0.300 |
| Tryptone | 0.500 |
| $CaCO_3$ | 0.200 |
| $CoCl_2$ | 0.0001 |
| $MgSO_47H_2O$ | 0.050 |
| NE-302 | 0.05 |

TABLE 9

Seed culture medium (SC)

| Ingrediant | Amount(%) |
|---|---|
| Glucose | 1.000% |
| Dextrin | 3.000% |
| Soytone | 1.000% |
| Corn seed meal | 0.500% |
| Yeast extract | 0.500% |
| $K_2HPO_4$ | 0.100% |
| $CaCO_3$ | 0.400% |
| $MgSO_47H_2O$ | 0.086% |
| $CaCl_2$ | 0.010% |
| $(NH_4)_2SO_4$ | 0.100% |
| Soybean oil | 0.080% |
| NE-302 | 0.080% |

TABLE 10

Main fermentation medium (MF)

| Ingredient | Amount(%) |
|---|---|
| Glucose | 2.000% |
| Soluble starch | 6.000% |
| Corn steep liquor | 1.600% |
| Corn seed meal | 0.600% |
| Yeast extract | 0.800% |
| Soytone | 1.250% |
| $CaCO_3$ | 0.300% |
| $K_2HPO_4$ | 0.100% |
| $MgSO_47H_2O$ | 0.086% |
| $CaCl_2$ | 0.010% |
| $FeSO_47H_2O$ | 0.001% |
| L-Valine | 0.050% |
| NE-302 | 0.050% |

For routine and reproducible processing, frozen vegetative mycelia (FVM) was prepared as follows; a single mycelium grown on ISP 3 medium for 7 days at 28° C. was inoculated into a 500 ml baffled flask containing 70 ml of SC medium and incubated at 34° C. with a shaking speed of 200 rpm for 3 days. The complete culture broth was thoroughly mixed with 50% glycerol and the vegetative mycelia-glycerol mixture was stored at −80° C. until use.

Figure 7:
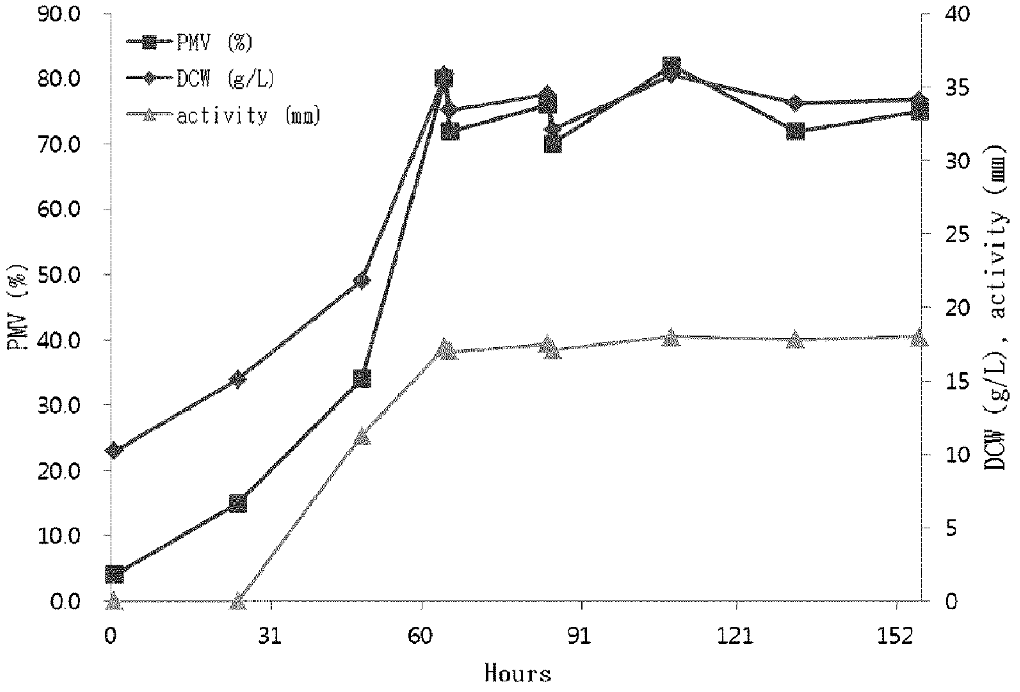
FIG. 7 shows the graph of biomass and activity of anti-TB compounds in main fermentation (DCW; dry cell weight, PMV; packed mycelium volume, activity; zone of growth inhibition against *Mycobacterium smegmatis* mc2155 by paper disk diffusion assay).

The FVM, at 10% v/v was used to initiate the activation culture. The activation stage was performed at 34° C. with a shaking speed of 200 rpm for 54 hours. Through this activation stage, the packed mycelium volume (PMV) was 15% and the pH was at 7.58. The young active vegetative culture broth was used for seed culture at 10% v/v. The second seed culture was maintained at 34° C. with a shaking speed of 200 rpm for 60 hours. The PMV and pH were 43%, 7.48, respectively. The seed culture broth was transferred to the main fermentation medium at 10% v/v. The main fermentation was performed at 34° C. with an agitation speed of 600 rpm and 0.3 vvm of aeration for 144 hours. The final PMV was 80% at pH 8.20 and total sugar was less than 1.8%. The fermentation process yielded 373 mg/L of H-14 (FIG. 7).

Example 5

Isolation of Novel Anti-TB Peptides, H-14 and H-16, from *Nonomuraea* sp. MJM5123

Isolation Example 1

Strain MJM5123, one of 20 prioritized actinomycete strains, was fermented in large scale and its active fractions were isolated in Example 1 by the method described below.

The large-scale mycelial methanolic extract of strain E5123 underwent a chemical fractionation process, in parallel with biological characterization using MABA, LORA and Vero cell toxicity to monitor the activity and selectivity index. Fractionation and isolation of active constituents involved three steps of chromatographic separation. Vacuum liquid chromatography (VLC) of the extract (128.7 g) on reversed phase silica gel using a water/methanol gradient in 20% steps yielded seven chemically distinct fractions, VC-1 to 7. MICs of <0.76, 0.74 μg/ml were observed for fractions VC-6 & 7 eluting with 100% methanol and 100% chloroform, respectively. VC-6 & 7 were recombined (8.47 g) and further separated into 81 fractions on a Sephadex LH-20 open column with 100% methanol as eluent, yielding a panel of 11 recombined fractions, S-1 to 11 (by TLC). MICs were <0.21 μg/ml for subfractions S-2 and S-3. S-3 (374 mg) was separated into 110 fractions by high speed countercurrent chromatography (HSCCC) with HEMWat+2 selected as the most suitable solvent system by the GUESS method [Kubo, I. Recent applications of counter-current chromatography to the isolation of bioactive natural products. *J Chrom* 1991, 538, 187-191]. These fractions were recombined to a panel of 11 fractions from H'-1 to H'-11. The MICs were <0.391 μg/ml for subfractions H-4, H-6, H-8, and H-9. S-2 (177 mg) was further separated into 140 fractions by HSCCC with HEMWat+2, and recombined to a panel of 26 fractions, H-1 to H-26. MICs were <0.5 μg/ml for H-3, H-5, H-7, H-9 to H-23. Among the active peptide fractions, H-14 and H-16 (8 mg, yield=0.4 mg/L) were the purest by qHNMR analysis and, therefore, selected for structural elucidation. After recombining H-11 to H-15 and H'-6 to H'-8 according to similarity of their $^{1}$HNMR spectra, 189 mg H-14 (approx. 80% pure) was obtained (yield=9.45 mg/L). The overall amount of active peptides is approx. 369 mg, yield=18 mg/L.

Isolation Example 2

The anti-TB compounds produced by fermentation of MJM5123 were mostly retained inside the cell. The anti-TB compounds were extracted from the mycelial cake; the latter was harvested from the fermentation procedure, as described above, by filtration of the entire fermentation broth. Extraction of the mycelial cake was the most effective with methanol, but other organic solvents such as ethanol, n-propanol, isopropanol, acetonitrile, acetone, dichloromethane, ethyl acetate, chloroform, and the like can be employed. The crude anti-TB active compounds were recovered from the extracting solution by routine process which includes evaporation of the extract to a suitable volume and solvent-solvent partitioning.

The methanol extract was concentrated in vacuo at 37° C. and deionized water was added into the concentrated solution to achieve 70% methanol. The water mixture was defatted by partitioning with n-hexane and the defatted solution diluted with one volume of deionized water. This was extracted with one volume of chloroform and the chloroform layer containing the anti-TB active compounds, was cleaned by shaking with deionized water. Dryness of the chloroform layer yielded a yellowish solid which was then dissolved in 100% methanol and applied to Sephadex™ LH-20 equilibrated with 100% methanol. The anti-TB active compounds were pooled by steric exclusion chromatography with 100% methanol elution. H-14 and H-16, demonstrating potent anti-TB activity, were fully purified by high performance liquid chromatography using a reverse-phase C-18 column and 35% aqueous acetonitrile solution buffered with 20 mM sodium phosphate (pH 8.0) as a mobile phase. Purified fractions were evaporated to remove acetonitrile and extracted with chloroform. Finally, the chloroform layers were concentrated to dryness and highly purified H-14 and H-16 were subjected to further study including structure determination and in vitro anti-TB activity.

Example 6

Structure Elucidation of Anti-TBs Cyclic Peptide H-14

H-14 is a metabolite of *Nonomuraea* sp. MJM5123 which is obtained by MeOH extraction of the mycelia. The molecular formula for H-14 is $C_{83}H_{134}O_{17}N_{14}$ as determined by $^{1}$H, $^{13}$C NMR and high resolution mass spectrometry.

H-14 was isolated as an optically active light yellow powder. The high resolution mass spectrum showed a positive ion peak $[M+H]^+$ at 1600.0189 m/z, and a positive ion peak $[M+Na]^+$ at 1621.9982 m/z, indicating an exact mass of 1599.0111. The IR spectrum suggested the presence of multiple amide moities (1632.16 $cm^{-1}$). The UV spectrum suggested H-14 being a peptide with aromatic residues, with absorption bands at 211 nm (=54209 $M^{-1}cm^{-}$, 48, 25° C., in methanol), 219 nm (=55266 $M^{-1}cm^{-1}$, 48, 25° C., in methanol), 263 nm (=7925 $M^{-1}cm^{-1}$, 48, 25° C., in methanol), 281 nm (=6465 $M^{-1}cm^{-1}$, 48, 25° C., in methanol), and 291 nm (=5839 $M^{-1}cm^{-1}$, 48, 25° C., in methanol). The CD spectrum suggested H-14 being a peptide of antiparallel β-sheet structure, with molar ellipticity of 1918530 $degcm^2mol^{-1}$ at 220 nm (25° C., in acetonitrile) and 616094 $degcm^2mol^{-1}$ at 196 nm (25° C., in acetonitrile).

Despite the relatively large size of this molecule, the NMR spectra showed acceptable signal dispersion and have therefore been a valuable source of structural information. The $^{1}$H NMR spectrum in methanol-$d_3$ displayed 8 exchangeable proton signals between 9.20 and 7.72 ppm that vanished upon exchange into fully-deuterated methanol. In addition, signals occurred in the aromatic region coding for one phenyl group and another aromatic system, and doublets were found at 0.73 to 1.33 ppm corresponding to 20 aliphatic methyl groups. Surprisingly for the case of a peptide, seven singlets at 2.16, 2.31, 3.14, 3.23, 3.26, 3.33, and 3.82 ppm appeared, indicating 8 N-methyl and/or methoxy groups, as a singlet at 2.31 ppm integrates for 2 methyl groups. The distribution of signals with doublets in the amide proton region and signals covering the complete range between 5.4 and 0.7 ppm was a clear indication that the investigated compound was indeed a peptide.

Further spectroscopic evidence supporting the classification of the compound as a peptide was derived from the $^{13}$C NMR spectrum, which revealed a total of 12 (amide-) carbonyl signals in the range between 170.92 and 175.14 ppm, corresponding to 13 carbonyl carbons. By using DEPT135 and HSQC experiments, 34 methine, 3 methylene, and 28 methyl signals were identified. These signals, along with 5 quaternary carbon signals at 155.23, 142.68, 140.04, 118.36, and 112.47 ppm indicated a total of 83 carbons present in H-14.

Extensive analysis of the 2D NMR spectra of H-14, particularly based on COSY, TOCSY, HSQC, HMBC and semi-selective HMBC experiments resulted in the elucidation of 15 discrete $^{1}$H, $^{1}$H spin systems: N,N-$Me_2$-Val, $Val^1$, N-Me-L-allo-Ile, L-Thr, N-Me-L-Thr, L-$Val^2$, N-Me-L-Leu, L-$Val^3$, N-Me-L-Val, N-Me-4-OMe-L-Trp a, N-Me-4-OMe-L-Trp b, L-$Val^4$, R-β-OH-L-Phe a, R-β-OH-L-Phe b and L-$Val^5$. The detailed $^{1}$H and $^{13}$C assignment is given in Table 11. The $^{13}$C and $^{1}$H signals of terminal methyl groups are in very crowded regions. The $^{13}C$ NMR spectra displayed 14 carbon signals representing 14 carbons within a 0.94 ppm window from 19.10 ppm and 20.04 ppm, and the $^{1}H$ NMR spectra displayed 17 proton signals representing 47 protons within a 0.14 ppm window from 0.85 ppm to 1.09 ppm. The resolution of HSQC and HMBC experiments are not high enough to establish connectivity for these signals, so we introduced the semi-selective HMBC experiment, which yields high-resolution in the indirect $^{13}C$ dimension by suppressing homonuclear proton coupling modulations. The direct H—C connectivity was built by using $^{13}C$—$^{1}H$ single bond correlations extracted from a semi-selective HMBC experiment. Such correlations were observed with a coupling constant around 126 Hz along the F2 direction. The methyl groups were connected to their spin systems respectively by using the $^{1}H$, $^{13}C$ long-range correlations between methyl proton signals and usually β-carbon signals, and methyl carbon signals and usually β-proton signals, extracted from a semi-selective HMBC experiment.

Connectivity inside the N-Me-4-OMe-L-Trp and R-β-OH-L-Phe units was established by using 1H, $^{13}C$ long-range correlations extracted from the HMBC experiment. Such HMBC correlations were observed for N-Me-4-OMe-L-Trp $H^{4}$/N-Me-4-OMe-L-Trp $C^{\beta}$, R-β-OH-L-Phe $H^{2'}$/R-β-OH-L-Phe $C^{\beta}$, and R-β-OH-L-Phe $H^{5'}$/R-β-OH-L-Phe $C^{\beta}$.

The position of the methoxy group of N-Me-4-OMe-L-Trp was also determined by analyzing HMBC correlations. HMBC correlations were observed for N-Me-4-OMe-L-Trp $H^{12}$/N-Me-4-OMe-L-Trp $C^{10}$, N-Me-4-OMe-L-Trp $H^{8}$/N-Me-4-OMe-L-Trp $C^{6}$, N-Me-4-OMe-L-Trp $H^{7}$/N-Me-4-OMe-L-Trp $C^{11}$, N-Me-4-OMe-L-Trp $H^{9}$/N-Me-4-OMe-L-Trp $C^{11}$.

The positions of N-methyl groups were determined by analyzing HMBC correlations. (i, i) $H^{NMe}$, Cα and/or (i, i−1) $H^{NMe}$, $C^{C=O}$ HMBC correlations were observed for N,N-$Me_2$-Val $H^{6(7)}$/N,N-$Me_2$-Val $C^{\alpha}$, N-Me-L-allo-Ile $H^{7}$/$Val^{1}$ $C^{C=O}$, N-Me-L-allo-Ile $H^{7}$/N-Me-L-allo-Ile $C^{\alpha}$, N-Me-L-Thr $H^{5}$/L-Thr $C^{C=O}$, N-Me-L-Thr $H^{5}$/N-Me-L-Thr $C^{\alpha}$, N-Me-L-Leu $H^{7}$/L-$Val^{2}$ $C^{C=O}$, N-Me-L-Leu $H^{7}$/N-Me-L-Leu $C^{\alpha}$, N-Me-L-Val $H^{6}$/L-$Val^{3}$ $C^{C=O}$, N-Me-L-Val $H^{6}$/N-Me-L-Val $C^{\alpha}$, N-Me-4-OMe-L-Trp $H^{13}$/N-Me-L-Val $C^{C=O}$, N-Me-4-OMe-L-Trp $H^{13}$/N-Me-4-OMe-L-Trp $C^{\alpha}$.

Most of the individual amino acid residues were subsequently linked sequentially via $^{1}H$, $^{13}C$-long range correlations, except the N,N-$Me_2$-Val and N-Me-L-Leu units. For each amino acid residue two correlations between $H^{\alpha}$, $C^{C=O}$ were observed, (i, i) $H^{\alpha}$, $C^{C=O}$ and (i, i−1) $H^{\alpha}$, $C^{C=O}$, which together determine the peptide bond connectivity; while only one correlation between $H^{\beta}$, $C^{C=O}$ is observed, which determines the carbonyl group of the residue. Again a semi-selective HMBC experiment was employed, as HMBC experiments cannot resolve the crowded carbonyl region with 13 $^{13}C$ signals presented in a 4.23 ppm window from 170.91 ppm to 175.14 Ppm. Correlations were observed for N,N-$Me_2$-Val $H^{\alpha}$/N,N-$Me_2$-Val $C^{C=O}$, N,N-$Me_2$-Val $H^{\beta}$/N,N-$Me_2$-Val $C^{C=O}$, $Val^{1}$ $H^{\alpha}$/$Val^{1}$ $C^{C=O}$, $Val^{1}$ $H^{\beta}$/$Val^{1}$ $C^{C=O}$, N-Me-L-allo-Ile $H^{\alpha}$/N-Me-L-allo-Ile $C^{C=O}$, N-Me-L-allo-Ile $H^{\alpha}$/$Val^{1}$ $C^{C=O}$, N-Me-L-allo-Ile $H^{\beta}$/N-Me-L-allo-Ile $C^{C=O}$, N-Me-L-allo-Ile $H^{\alpha}$/L-thr $C^{C=O}$, L-Thr $H^{\alpha}$/N-Me-L-allo-Ile $C^{C=O}$, L-Thr $H^{+}$/L-Thr $C^{C=O}$, N-Me-L-Thr $H^{\alpha}$/N-Me-L-Thr $C^{C=O}$, N-Me-L-Thr $H^{\alpha}$/L-Thr $C^{C=O}$, N-Me-L-Thr $H^{\beta}$/N-Me-L-Thr $C^{C=O}$, L-$Val^{2}$ $H^{\alpha}$/L-$Val^{2}$ $C^{C=O}$, L-$Val^{2}$ $H^{\alpha}$/N-Me-L-Thr $C^{C=O}$, L-$Val^{2}$ $H^{\beta}$/L-$Val^{2}$ $C^{C=O}$, N-Me-L-Leu $H^{\alpha}$/N-Me-L-Leu $C^{C=O}$, N-Me-L-Leu $H^{\alpha}$/L-$Val^{2}$ $C^{C=O}$, N-Me-L-Leu $H^{\beta}$/N-Me-L-Leu $C^{C=O}$, L-$Val^{3}$ $H^{\alpha}$/L-$Val^{3}$ $C^{C=O}$, L-$Val^{3}$ $H^{\beta}$/L-$Val^{3}$ $C^{C=O}$, N-Me-L-Val $H^{\alpha}$/N-Me-L-Val $C^{C=O}$, N-Me-L-Val $H^{\alpha}$/L-$Val^{3}$ $C^{C=O}$, N-Me-L-Val $H^{\beta}$/N-Me-L-Val $C^{C=O}$, N-Me-4-OMe-L-Trp $H^{\alpha}$/N-Me-4-OMe-L-Trp $C^{C=O}$, N-Me-4-OMe-L-Trp $H^{\alpha}$/N-Me-L-Val $C^{C=O}$, N-Me-4-OMe-L-Trp $H^{\beta}$/N-Me-4-OMe-L-Trp $C^{C=O}$, L-$Val^{4}$ $H^{\alpha}$/L-$Val^{4}$ $C^{C=O}$, L-$Val^{4}$ $H^{\alpha}$/N-Me-4-OMe-L-Trp $C^{C=O}$, L-$Val^{4}$ $H^{\beta}$/L-$Val^{4}$ $C^{C=O}$, R-β-OH-L-Phe $H^{\alpha}$/R-β-OH-L-Phe $C^{C=O}$, R-β-OH-L-Phe $H^{\alpha}$/L-$Val^{4}$ $C^{C=O}$, R-β-OH-L-Phe $H^{\beta}$/R-β-OH-L-Phe $C^{C=O}$, L-$Val^{5}$ $H^{\alpha}$/L-$Val^{5}$ $C^{C=O}$, L-$Val^{5}$ $H^{\alpha}$/R-β-OH-L-Phe $C^{C=O}$, L-$Val^{5}$ $H^{\beta}$/L-$Val^{5}$ $C^{C=O}$. The $^{13}C$ signals of carbonyl groups from $NMe_2$-Val and NMe-L-Leu were overlapping at 173.29 ppm, leaving the connectivity of $Val^{1}$ $H^{\alpha}$ and L-$Val^{3}$ $H^{\alpha}$ with carbonyl groups undetermined, thus leaving two possible structures for H-14.

In addition, a HMBC correlation between L-Thr $H^{\beta}$ and L-$Val^{5}$ $C^{C=O}$ was observed, suggesting H-14 to be a cyclic depsipeptide cyclized between the C-terminal carboxyl and the side chain of a L-Thr residue.

These data, together with a molecular weight of 1599.0111 as determined by high resolution mass spectrometry are consistent with the molecular formula $C_{83}H_{34}N_{14}O_{17}$.

However, the connection between N,N-$Me_2$-Val and L-$Val^{1}$ was confirmed with the analysis of the tandem mass spectrum of H-14 showing the fragment ion [N,N-$Me_2$-Val+L-$Val^{1}$+N-Me-L-allo-Ile$]^{+}$ at m/z 354.32.

The following fragments that helped to establish the sequence of the molecule were detected in the tandem mass spectrum: m/z (rel. int.) 1600.23 $[M+H]^{+}$ (8), 1246.95 [M-N,N-$Me_2$-Val-L-$Val^{1}$-N-Me-L-allo-Ile+2H$]^{+}$ (48), 990.86 [M-N,N-$Me_2$-Val-L-$Val^{1}$-N-Me-L-allo-Ile-L-Thr-L-$Val^{5}$+2H$]^{+}$ (7), 800.60 $[M+2H]^{2+}$ (50), 610.41 [N,N-$Me_2$-Val+L-$Val^{1}$+N-Me-L-allo-Ile+L-Thr+L-$Val^{5}]^{+}$ (36), 354.32 [N,N-$Me_2$-Val+L-$Val^{1}$+N-Me-L-allo-Ile$]^{+}$ (87).

TABLE 11

$^{1}H$ and $^{13}C$ NMR Data of H-14 in $CD_3OD$

| Amino Acid | | $^{1}H$ J (Hz) | $^{13}C$ | Amino Acid | | $^{1}H$ J (Hz) | $^{13}C$ |
|---|---|---|---|---|---|---|---|
| N,N-$Me_2$-Val | 1 | | 173.29 | L-$Val^{3}$ | 1 | | 173.39 |
| | 2 | 2.67 (d, 9.2) | 75.62 | | 2 | 4.59 (d, 8.9) | 55.34 |
| | 3 | 2.04 (ddd, 9.2, 6.6, 6.6) | 28.83 | | 3 | 2.03 (ddd, 8.9, 6.6, 6.8) | 32.88 |
| | 4 | 2.31 (s) | 42.24 | | 4 | 0.92 (d, 6.6) | |
| | 5 | 2.31 (s) | 42.24 | | 5 | 0.86 (d, 6.8) | |
| | 6 | 0.85 (d, 6.6) | 19.36 | | NH | 9.07 (d, 9.5) [b] | |
| | 7 | 0.98 (d, 6.6) | 20.04 | | | | |

TABLE 11-continued $^{1}$H and $^{13}$C NMR Data of H-14 in $CD_3OD$

| Amino Acid | | $^{1}$H J (Hz) | $^{13}$C | Amino Acid | | $^{1}$H J (Hz) | $^{13}$C |
|---|---|---|---|---|---|---|---|
| L-Val[1] | 1 | | 174.93 | N-Me-L-Val | 1 | | 170.91 |
| | 2 | 4.67 (d, 8.8) | 55.78 | | 2 | 3.07 (d, 7.6) | 71.37 |
| | 3 | 2.10 (ddd, 8.8, 6.8, 6.7) | 31.65 | | 3 | 2.58 (ddd, 7.6, 6.5, 6.8) | 30.3 |
| | 4 | 0.99 (d, 6.8) | 19.61 | | 4 | 0.98 (d, 6.8) | |
| | 5 | 1.06 (d, 6.7) | 19.36 | | 5 | 1.09 (d, 6.5) | 22.04 |
| | NH | 8.17 (d, 8.2) [b] | | | 6 | 3.14 (s) | 40.5 |
| N-Me-L-allo-Ile | 1 | | 172.62 | N-Me-4-OMe-L-Trp | 1 | | 171.62 |
| | 2 | 4.92 (d, 11.2) | 59.24 | | 2 | 4.10 (dd, 11.2, 4.7) | 71.09 |
| | 3 | 1.95 (dddd, 11.2, 0.5, 2.9, 6.6) | 34.32 | | 3 | 3.54 (dd, 11.2, −13.7) | 26.79 |
| | 4 | 0.99 (ddd, 0.5, −12.2, 7.3) | 26.61 | | | 3.69 (dd, 4.7, −13.7) | |
| | | 1.26 (ddd, 2.9, −12.2, 7.6) | | | 4 | | 112.5 |
| | 5 | 0.75 (dd, 7.3, 7.6) | 11.48 | | 5 | 6.69 (d, 2.0, 0.5) | 124.1 |
| | 6 | 0.74 (d, 6.6) | 15.09 | | NH | 10.22 (d, 2.0) | |
| | 7 | 3.23 (s) | 31.40 | | 6 | | 140 |
| | | | | | 7 | 6.92 (d, 0.5, 0.7, 8.2) | 106.12 |
| | | | | | 8 | 6.98 (dd, 8.2, 7.8) | 123.39 |
| | | | | | 9 | 6.44 (d, 0.7, 7.8) | 99.89 |
| | | | | | 10 | | 155.2 |
| | | | | | 11 | | 118.4 |
| | | | | | 12 | 3.83 (s) | 55.62 |
| | | | | | 13 | 2.16 (s) | 40.98 |
| L-Thr | 1 | | 171.95 | L-Val[4] | 1 | | 174.14 |
| | 2 | 5.17 (d, 2.3) | 53.57 | | 2 | 4.53 (d, 7.9) | 59.29 |
| | 3 | 5.78 (dd, 2.3, 6.5) | 69.84 | | 3 | 2.20 (ddd, 7.9, 6.7, 6.8) | 33.73 |
| | 4 | 1.31 (d, 6.5) | 16.76 | | 4 | 1.03 (d, 6.7) | |
| | NH | 8.50 (d, 9.1) [b] | | | 5 | 0.99 (d, 6.8) | |
| | | | | | NH | 7.85 (d, 9.6) [b] | |
| N-Me-L-Thr | 1 | | 171.21 | R-β-OH-L-Phe | 1 | | 173.76 |
| | 2 | 5.02 (d, 3.7) | 62.90 | | 2 | 4.85 (d, 1.9) | 59.78 |
| | 3 | 4.46 (dd, 3.7, 6.5) | 66.90 | | 3 | 5.34 (d, 1.9) | 72.96 |
| | 4 | 0.91 (d, 6.5) | 19.91 | | 4 | | 142.8 |
| | 5 | 3.33 (s) | 34.32 | | 5, 9 | 7.26[a] | 127.17 |
| | | | | | 6, 8 | 7.24[a] | 129.39 |
| | | | | | 7 | 7.20[a] | 128.28 |
| | | | | | NH | 8.30 (d, 7.8) [b] | |
| L-Val[2] | 1 | | 174.45 | L-Val[5] | 1 | | 175.14 |
| | 2 | 4.84 (d, 8.9) | 56.78 | | 2 | 4.40 (d, 8.9) | 59.22 |

TABLE 11-continued

| $^1H$ and $^{13}C$ NMR Data of H-14 in $CD_3OD$ | | | | | | | |
|---|---|---|---|---|---|---|---|
| Amino Acid | | $^1H$ J (Hz) | $^{13}C$ | Amino Acid | | $^1H$ J (Hz) | $^{13}C$ |
| | 3 | 2.35 (ddd, 8.9, 6.7, 7.0) | 31.78 | | 3 | 1.97 (m, 8.9, 6.8, 6.4) | 33.19 |
| | 4 | 1.09 (d, 6.7) | 19.64 | | 4 | 0.92 (d, 6.4) | 19.10 |
| | 5 | 0.98 (d, 7.0) | 19.70 | | 5 | 0.93 (d, 6.8) | 19.44 |
| | NH | 7.73 (d, 8.6) [b] | | | NH | 9.02 (d, 9.9) [b] | |
| N-Me-L-Leu | 1 | | 173.28 | | | | |
| | 2 | 5.11 (dd, 6.2, 8.4) | 55.59 | | | | |
| | 3 | 1.24 (ddd, 8.4, −13.3, 5.8) 1.45 (ddd, 6.2, −13.3, 8.2) | 39.33 | | | | |
| | 4 | 0.96 (dddd, 8.2, 5.8, 6.5, 6.6) | 25.64 | | | | |
| | 5 | 0.17 (d, 6.6) | 21.69 | | | | |
| | 6 | 0.33 (d, 6.5) | 23.48 | | | | |
| | 7 | 3.26 (s) | 31.63 | | | | |

[a]Multiplicity of the signals is unclear due to overlapping.
[b] Data obtained from $^1H$ NMR experiment in methanol-$d_3$.

Figure 11:
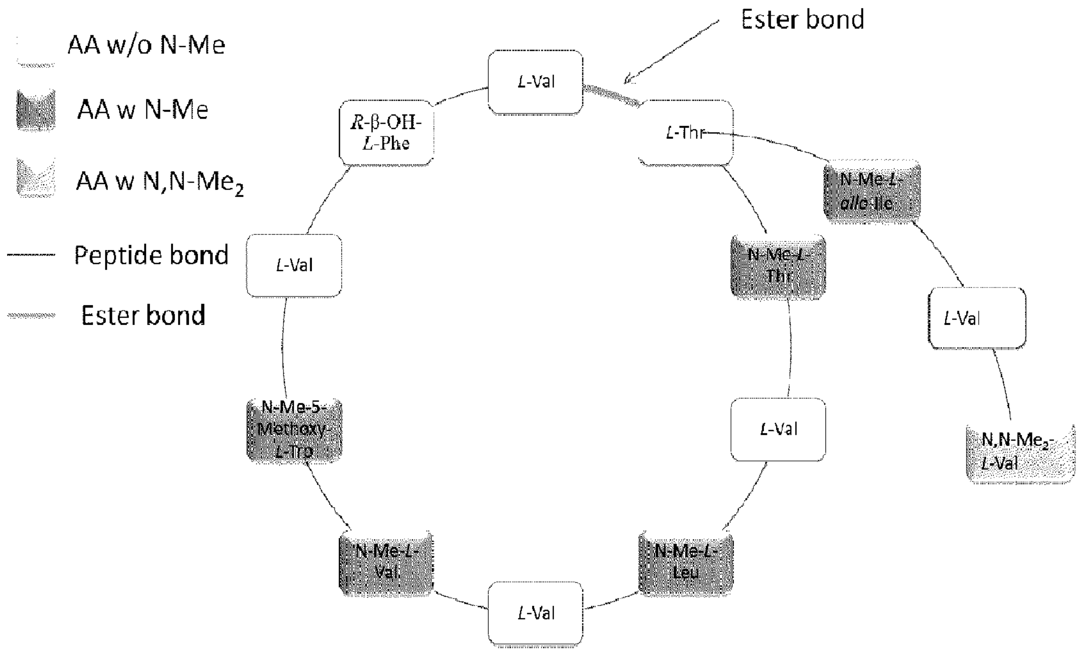
FIG. 11 shows the structural arrangement of the cyclic H-14 peptide of the present invention.

Structure of the H-14 isolated and purified from MJM5123 (*Nonomuraea* sp.) is shown in formula 1. FIG. 11 shows the structural arrangement of the cyclic H-14 peptide.

Crystallization and Structure Determination

A needle shaped crystal of H-14 was obtained from MeOH: MeCN:Water=(1:1:0.5) using a slow evaporation method

[Formula 1]

Figure 8:
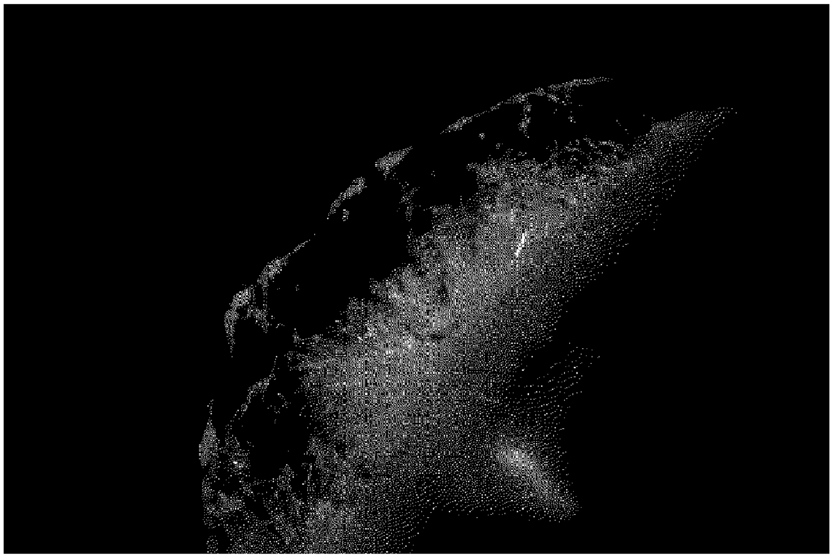
FIG. 8 shows crystals of H-14 grown using a slow evaporation method. The longest dimension was approximately 0.5 mm.

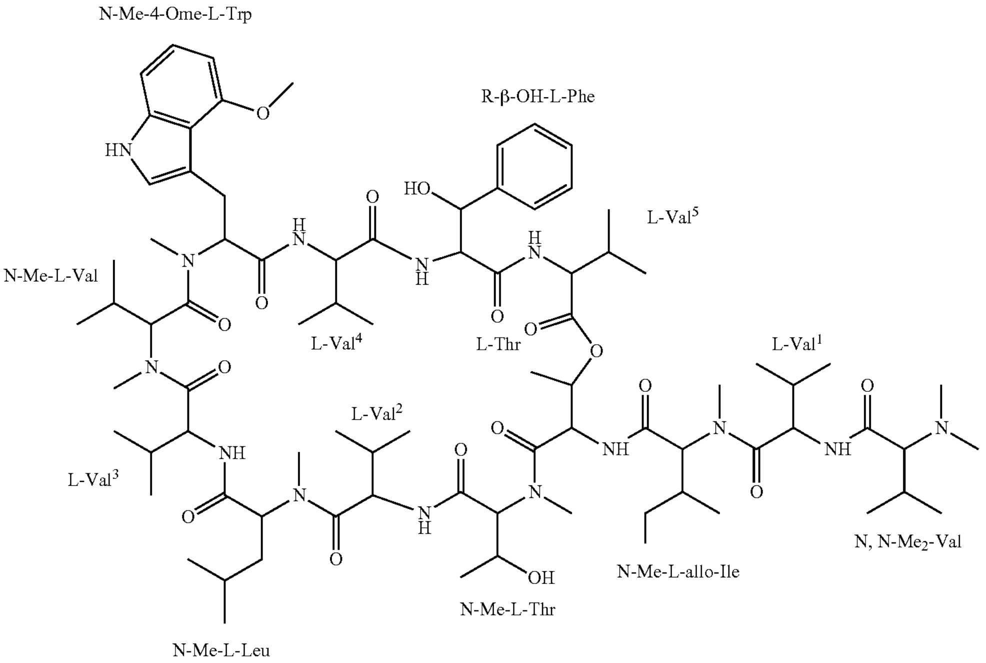

over 57 days. Crystal dimensions were approximately 0.1×0.15×0.5 mm. X-ray data were collected at room temperature on a Bruker D8 discover x-ray system and the crystal diffracted X-ray to 0.83 The crystal belonged to orthorhombic space group P2(1)2(1)2 with unit cell parameters, a=71.64, b=11.43, c=12.70 There is one molecule in the asymmetric unit (FIG. 8 and Table 12).

TABLE 12

| Data collection statistics | |
|---|---|
| X-ray Wavelength (Å) | Mo Ka (λ = 0.71073 Å) (Bruker) |
| Temperature (K) | 296.15 |
| Space group | $P2_12_12$ |
| Unit-cell parameters (Å) | a = 71.64 Å<br>b = 11.43 Å<br>c = 12.70 Å |
| Resolution limit (Å) | 0.83 |

Figure 9:
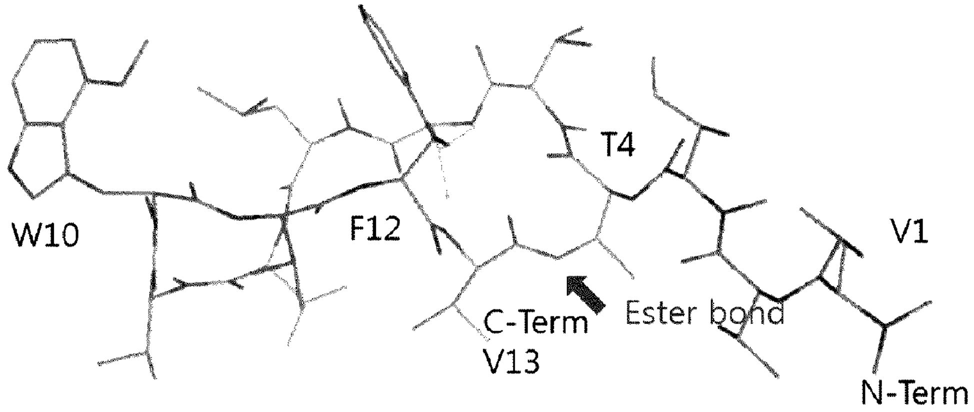
FIG. 9 shows a 3D structure of H-14.
Figure 10:
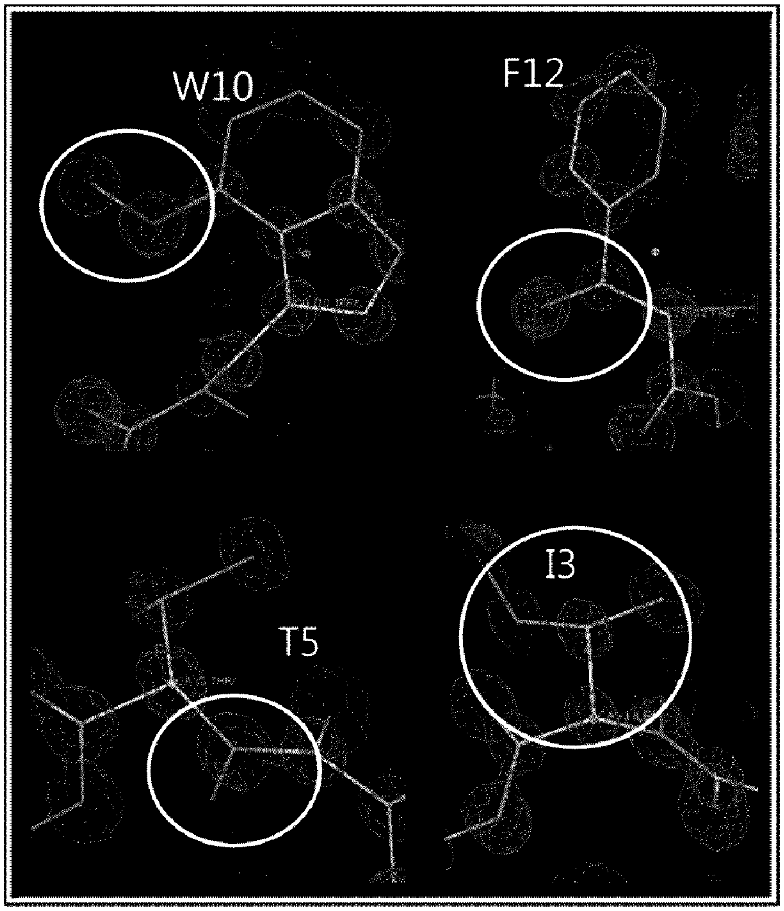
FIG. 10 shows an electron density map of selected residues, tryptophan (W10), phenylalanine (F12), threonine (T5) and isoleucine (I3) at 0.83 resolution.

The phase problem was solved by iterative dual-space direct methods starting with a random distribution of atoms using ShelxD software. The initial model generated from ShelxD was corrected according to the 2D structure of H-14 and water molecules were added guided by an initial electron density map generated with a graphic program, WinCoot. Finally, a refined model was obtained by reducing the R-factor to 0.1723 with refinement programs ShelxL or Refmac. As shown in FIG. 9, the overall structure of H-14 is similar to a twist hairpin-like anti-parallel structure. Five H-bonds between the C═O and N—H groups of the main chain stabilize the overall structure. Additionally, surrounding water molecules also participate in H-bond formation. From this X-ray structure and the result of Marfey's method (data not shown), we concluded that H-14 consists of all L amino acid or their analogs. All of the non-standard amino acid suggested by NMR analysis were also confirmed by inspecting the position of each atom using the electron density map (FIG. 9 and FIG. 10).

Example 7

Structure Elucidation of Anti-TB Cyclic Peptide H-16

H-16 is another metabolite of *Nonomuraea* sp. M5123. which is obtained from the MeOH extract of the mycelia. The molecular formula for H-16 is $C_{83}H_{134}O_{16}N_{14}$ as determined by $^{1}$H, $^{13}$C NMR and high resolution mass data.

H-16 was obtained as a light yellow amorphous powder. [The high resolution mass spectrum showed a positive ion peak $[M+H]^+$ at 1584.0227 m/z, and a positive ion peak $[M+Na]^+$ at 1606.0035 m/z, indicating an exact mass of 1583.0149. The high resolution mass spectrum and $^{13}$C NMR data were consistent with the molecular formula $C_{83}H_{134}N_{14}O_{16}$. The $^{1}$H NMR data indicated H-16 to be a peptide as well. The detailed $^{1}$H and $^{13}$C assignment is given in Table 13. The NMR spectroscopic identification of H-16 was performed analogously to that of H-14. In the process the spin systems of the amino acid residues were again identified by interpretation of the 2D NMR spectra, including COSY, TOCSY, HSQC and HMBC spectra. The individual amino acid residues were unambiguously linked sequentially through HMBC and semi-selective HMBC correlations. Such correlations were observed for N,N-Me$_2$-Val H$^{\alpha}$/N,N-Me$_2$-Val C$^{C=O}$, N,N-Me$_2$-Val H$^{\beta}$/N,N-Me$_2$-Val C$^{C=O}$, Val$^1$ H$^{\alpha}$/Val$^1$ C$^{C=O}$, Val$^1$ H$^{\alpha}$/N,N-Me$_2$-Val C$^{C=O}$, Val$^1$ H$^{\beta}$/Val$^1$ C$^{C=O}$, N-Me-Ile H$^{\alpha}$/N-Me-Ile C$^{C=O}$, N-Me-Ile H$^{\alpha}$/Val$^1$ N-Me-Ile H$^{\beta}$/N-Me-Ile C$^{C=O}$, Thr H$^{\alpha}$/Thr C$^{C=O}$, Thr H$^{\alpha}$/N-Me-Ile C$^{C=O}$, Thr H$^{\beta}$/Thr C$^{C=O}$, N-Me-Thr H$^{\alpha}$/N-Me-Thr C$^{C=O}$, N-Me-Thr H$^{\alpha}$/Thr C$^{C=O}$, N-Me-Thr H$^{\beta}$/N-Me-Thr C$^{C=O}$, Val$^2$ H$^{\alpha}$/Val$^2$ C$^{C=O}$, Val$^2$ H$^{\alpha}$/N-Me-Thr C$^{C=O}$, Val$^2$ H$^{\beta}$/Val$^2$ C$^{C=O}$, N-Me-Leu H$^{\alpha}$/N-Me-Leu C$^{C=O}$, N-Me-Leu H$^{\alpha}$/Val$^2$ C$^{C=O}$, N-Me-Leu H$^{\beta}$/N-Me-Leu C$^{C=O}$, Val$^3$ H$^{\alpha}$/Val$^3$ C$^{C=O}$, Val$^3$ H$^{\alpha}$/N-Me-Leu C$^{C=O}$, Val$^3$ H$^{\beta}$/Val$^3$ C$^{C=O}$, N-Me-Val H$^{\alpha}$/N-Me-Val C$^{C=O}$, N-Me-Val H$^{\alpha}$/Val$^3$ C$^{C=O}$, N-Me-Val H$^{\beta}$/N-Me-Val C$^{C=O}$, N-Me-4-OMe-Trp H$^{\alpha}$/N-Me-4-OMe-Trp C$^{C=O}$, N-Me-4-OMe-Trp H$^{\alpha}$/N-Me-Val C$^{C=O}$, N-Me-4-OMe-Trp H$^{\beta}$/N-Me-4-OMe-Trp C$^{C=O}$, Val$^4$ H$^{\alpha}$/Val$^4$ C$^{C=O}$, Val$^4$ H$^{\alpha}$/N-Me-4-OMe-Trp C$^{C=O}$, Val$^4$ H$^{\beta}$/Val$^4$ C$^{C=O}$, Phe H$^{\alpha}$/Phe C$^{C=O}$, Phe H$^{\alpha}$/Val$^4$ C$^{C=O}$, Phe H$^{\beta}$/Phe C$^{C=O}$, Val$^5$ H$^{\alpha}$/Val$^5$ C$^{C=O}$, Val$^5$ H$^{\alpha}$/Phe C$^{C=O}$, Val$^5$ H$^{\beta}$/Val$^5$ C$^{C=O}$.

TABLE 13

$^{1}$H and $^{13}$C NMR Data of H-16 in $CD_3OD$

| Amino Acid | | $^{1}$H J (Hz) | $^{13}$C | Amino Acid | | $^{1}$H J (Hz) | $^{13}$C |
|---|---|---|---|---|---|---|---|
| N,N-Me$_2$-Val | 1 | | 173.35 | L-Val$^3$ | 1 | | 173.63 |
| | 2 | 2.67 (d, 8.8) | 75.78 | | 2 | 4.59 (d, 9.2) | 55.59 |
| | 3 | 2.07 (m) | 28.49 | | 3 | 2.04 (m) | 32.74 |
| | 4 | 2.32 (s) | 42.40 | | 4 | 0.97 (d, 6.2) | 19.66 |
| | 5 | 2.32 (s) | 42.40 | | 5 | 0.87 (d, 6.5) | 19.40 |
| | 6 | 0.85 (d, 6.6) | 19.36 | | | | |
| | 7 | 0.98 (d, 6.6) | 20.12 | | | | |
| Val$^1$ | 1 | | 174.96 | N-Me-Val | 1 | | 171.09 |
| | 2 | 4.66 (d, 8.5) | 55.76 | | 2 | 3.06 (d, 7.4) | 71.60 |
| | 3 | 2.08 (m) | 31.57 | | 3 | 2.61 (m) | 31.57 |
| | 4 | 0.99 (d, 6.8) | 19.61 | | 4 | 0.97 (d, 6.2) | 19.75 |

TABLE 13-continued

| $^1H$ and $^{13}C$ NMR Data of H-16 in $CD_3OD$ | | | | | | | |
|---|---|---|---|---|---|---|---|
| Amino Acid | | $^1H$ J (Hz) | $^{13}C$ | Amino Acid | | $^1H$ J (Hz) | $^{13}C$ |
| | 5 | 1.06 (d, 6.7) | 19.36 | | 5 | 1.10 (d, 6.6) | 22.04 |
| | | | | | 6 | 3.13 (s) | 40.51 |
| N-Me-Ile | 1 | | 172.86 | N-Me-4-OMe-Trp | 1 | | 171.57 |
| | 2 | 4.94 (d, 11.7) | 61.60 | | 2 | 4.09 (dd, 10.8, 4.1) | 71.09 |
| | 3 | 1.96 (m) | 34.42 | | 3 | 3.56 (dd, 10.8, 13.5) | 22.87 |
| | 4 | 1.00 (m) | 26.36 | | | 3.70 (dd, 4.1, 13.5) | |
| | | 1.25 (m) | | | 4 | | 113.30 |
| | 5 | 0.72, (t, 7.7) | 19.36 | | 5 | 6.70 (d, 2.0) | 124.90 |
| | 6 | 0.75 (d, 5.2) | 15.19 | | NH | 10.22 (d, 2.0) | |
| | 7 | 3.24 (s) | 31.52 | | 6 | | 140.90 |
| | | | | | 7 | 6.92 (d, 8) | 107.00 |
| | | | | | 8 | 6.98 (dd, 8, 7.8) | 124.30 |
| | | | | | 9 | 6.44 (d, 7.8) | 100.80 |
| | | | | | 10 | | 156.00 |
| | | | | | 11 | | 118.90 |
| | | | | | 12 | 3.82 (s) | 55.74 |
| | | | | | 13 | 2.16 (s) | 41.92 |
| Thr | 1 | | 171.92 | Val[4] | 1 | | 174.11 |
| | 2 | 5.13 (d, 2.5) | 53.37 | | 2 | 4.40 (d, 8.5) | 59.17 |
| | 3 | 5.76 (dd, 2.5, 6.3) | 70.80 | | 3 | 2.19 (m) | 33.62 |
| | 4 | 1.32 (d, 6.7) | 17.80 | | 4 | 0.98 (d, 6.5) | 19.44 |
| | | | | | 5 | 1.04 (d, 6.9) | 19.96 |
| N-Me-Thr | 1 | | 171.42 | Phe | 1 | | 174.29 |
| | 2 | 5.04 (d, 3.6) | 63.92 | | 2 | 4.78 (dd, 2.1, 10.4) | 58.25 |
| | 3 | 4.44 (m) | 67.83 | | 3 | 3.37 (dd, 2.1, 15.0) | 38.20 |
| | 4 | 1.10 (d, 6.6) | 20.76 | | | 2.84 (dd, 10.4, 15.0) | |
| | 5 | 3.33 (s) | 35.28 | | 4 | | 140.90 |
| | | | | | 5, 9 | 7.09 (d, 7.0) | 131.22 |
| | | | | | 6, 8 | 7.21 (dd, 7.0, 7.55) | 130.47 |
| | | | | | 7 | 7.15 (d, 7.5) | 128.30 |
| Val[2] | 1 | | 174.93 | Val[5] | 1 | | 175.45 |
| | 2 | 4.82 (d, 9.5) | 56.87 | | 2 | 4.36 (d, 9.2) | 59.36 |
| | 3 | 2.40 (m) | 31.84 | | 3 | 1.97 (m) | 33.62 |
| | 4 | 1.09 (d, 6.7) | 19.64 | | 4 | 1.04 (d, 6.9) | 19.30 |
| | 5 | 0.98 (d, 7.0) | 19.70 | | 5 | 0.98 (d, 6.5) | 19.44 |
| N-Me-Leu | 1 | | 173.54 | | | | |
| | 2 | 5.15 (dd, 6.3, 8.4) | 56.80 | | | | |
| | 3 | 1.27 (m) 1.43 (m) | 40.50 | | | | |
| | 4 | 0.97 (m) | 26.52 | | | | |
| | 5 | 0.21 (d, 6.6) | 21.96 | | | | |
| | 6 | 0.32 (d, 6.2) | 23.54 | | | | |
| | 7 | 3.25 (s) | 31.63 | | | | |

Figure 12:
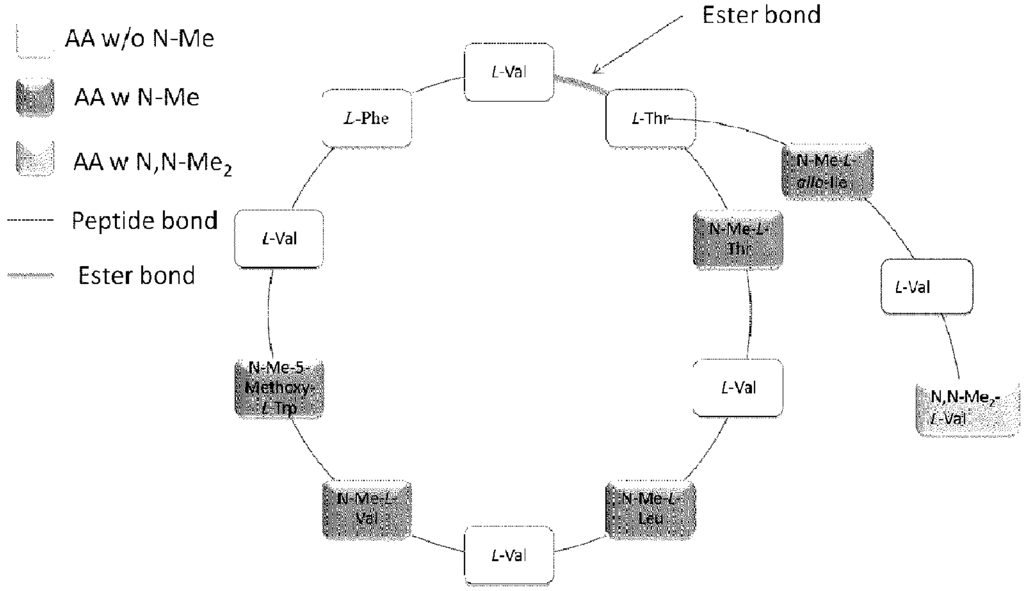
FIG. 12 shows the structural arrangement of the cyclic H-16 peptide of the present invention.
Figure 13:
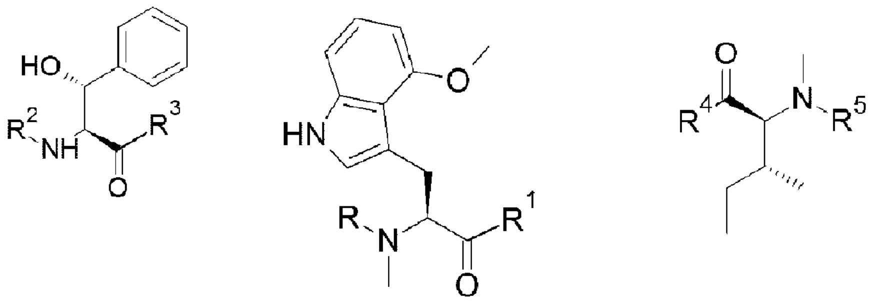
FIG. 13 shows the special amino acid residues in FIGS. 15 and 16.

Structure of H-16 isolated and purified from MJM5123 is shown in formula 2. FIG. 12 shows the structural arrangement of the cyclic H-14 peptide

[Formula 2]

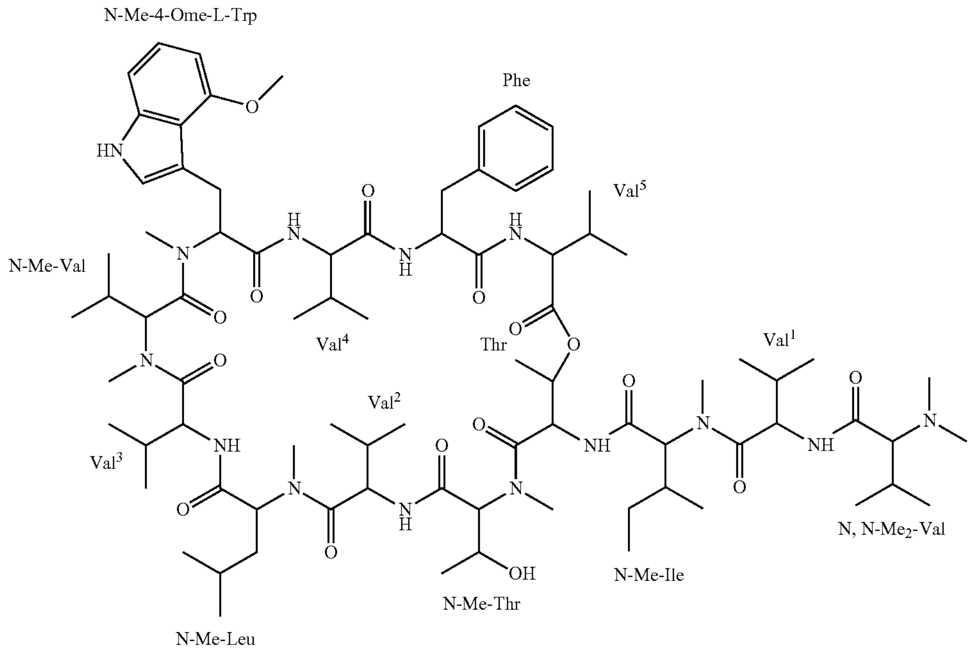

Experimental Example 1

MIC and MBC of H-14 and H-16 Against *M. tuberculosis* Under Aerobic Conditions

The inhibitory activity of H-14 and H-16 against *M. tuberculosis* was determined using Microplate Alamar Blue assay [Collins, L. and S. G. Franzblau, *Microplate alamar blue assay versus BACTEC* 460 *system for high-throughput screening of compounds against Mycobacterium tuberculosis and Mycobacterium avium*. Antimicrob Agents Chemother, 1997. 41(5): p. 1004-9; Hurdle, J. G., et al., *A microbiological assessment of novel nitrofuranylamides as anti-tuberculosis agents*. J Antimicrob Chemother, 2008. 62(5): p. 1037-45]. The MIC (minimum inhibitory concentration required to inhibit growth by 90%) and $MBC_{99}$ (minimum concentration that kills 99% of organisms) values for H-14 and H-16 measured under aerobic condition with the reference strain *M. tuberculosis* $H_{37}Rv$ are shown in Table 14.

The $MBC_{99}$ of each compound is only approximately two-fold higher than their MIC, thus H-14 and H-16 should be classified as bactericidal.

TABLE 14

Aerobic MIC and MBC against *M. tuberculosis* $H_{37}Rv$

| | H-14 | H-16 |
|---|---|---|
| MIC (μM) | 0.16 | 0.16 |
| $MBC_{99}$ (μM) | 0.34 | 0.19 |

*M. tuberculosis* is a clonal organism, which does not exchange genetic information from cell to cell. During the course of co-evolution with humans, a number of distinct lineages, or clades, have been generated and are prominent in various parts of the globe [Filliol, I., et al., *Global phylogeny of Mycobacterium tuberculosis based on single nucleotide polymorphism* (*SNP*) *analysis: insights into tuberculosis evolution, phylogenetic accuracy of other DNA fingerprinting systems, and recommendations for a minimal standard SNP set*. J Bacteriol, 2006. 188(2): p. 759-72; Gagneux, S. and P. M. Small, *Global phylogeography of Mycobacterium tuberculosis and implications for tuberculosis product development*. Lancet Infect Dis, 2007. 7(5): p. 328-37].

Table 15 presents the MICs of H-14 and H-16 against six *M. tuberculosis* strains representing geographic/genetic diversity, with the $H_{37}Rv$ laboratory strain as a reference. MICs of H-14 and H-16 against these six strains are comparable with their MICs against wild type $H_{37}Rv$, suggesting they will be broadly efficacious.

TABLE 15

MICs against Genetically/Geographically Diverse Clinical-Isolates of *M. tuberculosis* Clades

| | *M. tuberculosis* Clade | Geographical Location | Strain Code | MIC (μM) H-14 | MIC (μM) H-16 |
|---|---|---|---|---|---|
| MIC(μM) | $H_{37}Rv$ | | $H_{37}Rv$ | 0.38 | 0.37 |
| vs. | IndoOceanic | East Africa, South East Asia, South India | X003899 | 0.23 | 0.19 |
| | East Asian | East Asia, | X004439 | 0.29 | 0.19 |
| | | Russia, South Africa | X004244 | 0.13 | 0.09 |
| | Euro-American | Americas, | X005282 | 0.14 | 0.14 |
| | | Europe, North Africa, Middle East | X005319 | 0.36 | 0.34 |
| | East African Indian | East Africa, North India, Pakistan | X001354 | 0.38 | 0.37 |

Experimental Example 2

MBC of H-14 and H-16 Against *M. tuberculosis* Under Low Oxygen

The bactericidal activity of H-14 and H-16 against nonreplicating *M. tuberculosis* under low oxygen was determined by using the low oxygen recovery assay (LORA) [Cho, S. H., et al., *Low-oxygen-recovery assay for high-throughput screening of compounds against nonreplicating Mycobacterium tuberculosis*. Antimicrob Agents Chemother, 2007. 51(4): p. 1380-5] with cfu readout. The concentration effecting a 99% reduction in viability of *M. tuberculosis* after 10 days incubation under non-replicating conditions was approximately 1.5 μM for both H-14 and H-16. This low MBC suggests that H-14 and H-16 have potential in reducing the TB treatment duration by inhibiting a subpopulation of non-replicating persistors.

Experimental Example 3

Antibacterial Selectivities of H-14 and H-16

Selectivities of H-14 and H-16 were determined by screening them against *Escherichia coli*, a Gram-negative bacterium, *Staphylococcus aureus*, a Gram-positive bacterium, *Candida albicans*, a yeast, and six mycobacterial species (Table 16). Neither of the compounds displayed antimicrobial activity against *E. coli, S. aureus*, and *C. albicans*. Both compounds are active against *M. kansasii* with MICs below 0.4 μM, against *M. avium* with MICs below 1.0 μM, against *M. chelonae* and *M. marinum* with MICs below 2.0 μM, against *M. smegmatis* with MICs below 4.0 μM, but are significantly less active against *M. abscesses*. The results suggest H-14 and H-16 are selective anti-mycobacterial compounds.

TABLE 16

MICs against Other Mycobacterial Species, and Prototypical Gram-Positive, Gram-Negative and Yeast Species (Data from UIC)

| | MIC (μM) vs. | | | | | | | | |
|---|---|---|---|---|---|---|---|---|---|
| | *E.* | *S.* | *C.* | *Mycobacterium* | | | | | |
| | *Coli* | *aureus* | *albicans* | *Ssmegmatis* | *Chelonae* | *Abscesssus* | *Kansasii* | *avium* | *marinum* |
| H-14 | >32 | >32 | >32 | 1.74 | 0.97 | >63 | <0.24 | 0.35 | 0.95 |
| H-16 | >32 | >32 | >32 | 3.64 | 1.82 | >32 | <0.12 | 0.55 | 0.97 |

Experimental Example 4

Protein Binding and Toxicity Against Mammalian Cells

Protein binding may affect the pharmacokinetics of a compound and ultimately affect its efficiency by reducing the amount of active unbound compound. MICs of H-14 and H-16 against *M. tuberculosis* were determined in the presence of 10% fetal bovine serum (FBS), 4% bovine serum albumin (BSA) and without additional supplemental protein (0.4% BSA) as reference (Table 17). In the presence 10% FBS or 4% BSA, MICs increased by only 2-fold, suggesting protein binding should not adversely influence their efficacy.

TABLE 17

Effect of Protein Binding on MICs, measured with *M. tuberculosis* $H_{37}Pv$ (Data from UIC)

| | MIC vs. M. tuberculosis (μM) | | |
|---|---|---|---|
| | 0.5% BSA | 4% BSA | 10% BSA |
| H-14 | 0.16 | 0.58 | 0.36 |

Cytoxicities of H-14 and H-16 against mammalian cells were evaluated by testing against Vero cells, an African green monkey kidney cell line (Table 18). No cytoxicity was found for either compound at even the highest testing concentration (32 μM).

TABLE 18

Toxicity against Mammalian Cells

| | Vero cell $IC_{50}$ (μM) | Selectivity Index (SI) |
|---|---|---|
| H-14 | >32 | >620 |
| H-16 | >32 | >620 |

Experimental Example 5

MIC of H-14 and H-16 Against a Panel of Laboratory Generated Mono-Drug-Resistant *M. tuberculosis* Strains H-14 and H-16 were tested against a panel of $H_{37}Rv$-isogenic *M. tuberculosis* strains resistant to rifampin (RMP), isoniazid (INH), moxifloxacin (Mox), streptomycin (SM), kanamycin (KM), cycloserine (CS), or capreomycin (CAP) respectively (Table 19). Both compounds maintained their level of activity against all these mono-drug-resistant *M. tuberculosis* strains, suggesting no cross-resistance with current anti-TB drugs, and therefore a novel mode of action which will be equally suited for use against drug-sensitive and drug-resistant *M. tuberculosis* infections.

TABLE 19

| MICs against Laboratory-Generated Mono-Drug-Resistant *M. tuberculosis* Strains (Data from UIC) | | | | | | | | |
|---|---|---|---|---|---|---|---|---|
| | MIC (μM) vs. | | | | | | | |
| | | *M. tuberculosis* strains resistant to: | | | | | | |
| | $H_{37}Rv$ | RMP | INH | MOX | SM | KM | CS | CAP |
| H-14 | 0.16 | 0.19 | <0.12 | 0.31 | <0.12 | <0.12 | <0.12 | 0.29 |
| H-16 | 0.16 | 0.18 | <0.12 | 0.3 | <0.12 | <0.12 | <0.12 | 0.3 |

In conclusion, both H-14 and H-16 have in vitro anti-TB activity profiles comparable to, if not better than, current first line anti-TB drugs, with no in vitro mammalian cell toxicity at 100-fold their MBC. MICs against replicating *M. tuberculosis* are 0.16 μM, 0.16 μM, 0.09 μM and 0.47 μM for H14, H16, rifampin and isoniazid, respectively. The selectivity indexes (VERO cell $IC_{50}$/*M. tuberculosis* MIC) of H-14 and H-16 are both >620. This level of activity is maintained against isogenic strains of *M. tuberculosis* resistant to rifampin, isoniazid, streptomycin, kanamycin, cycloserine, and against the cyclic peptide, capreomycin, as well as to clinical isolates representative of global clades. MBCs against replicating *M. tuberculosis* are 0.34 μM and 0.19 μM for H-14 and H-16, respectively, indicating that both are strong bactericidal agents. Both compounds reduce viability of non-replicating *M. tuberculosis* by one $\log_{10}$ at approximately 1.5 μM in the LORA suggesting the potential to reduce TB treatment duration by inhibiting a subpopulation of *M. tuberculosis* persistors. In contrast, no activity was observed against *S. aureus, E. coli, C. albicans* at 31 μM, and activity was lower against *M. smegmatis*, implying that the anti-TB activity of both peptides is highly selective. This also suggests that these peptides would not have been originally detected by screening against surrogate bacteria. Protein binding should not adversely influence their efficacy, as MICs only increased two-fold in the presence of 4% BSA or 10% FBS.

The invention claimed is:

1. A crystalline pharmaceutical composition for the prevention or treatment of a *Mycobacterium* spp. related disease comprising a compound of Formula 1 and/or Formula 2 as an active ingredient in association with a pharmaceutically acceptable carrier, diluent, or excipient:

[Formula 1: H-14]

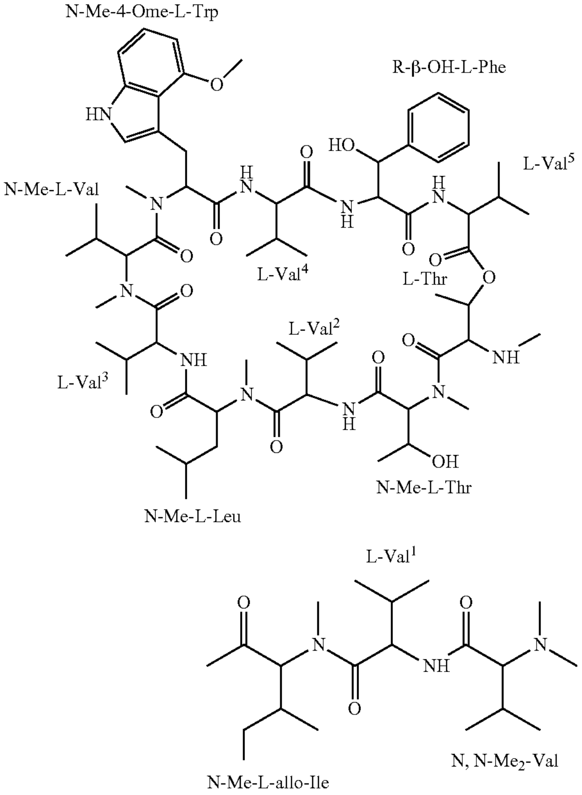

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: forward primer, 27f, for the amplification of
      16S rDNA from MJM5123 genomic DNA

<400> SEQUENCE: 1

agagtttgat cctggctcag                                                  20


<210> SEQ ID NO 2
<211> LENGTH: 19
<212> TYPE: DNA
<213> ORGANISM: Artificial
<220> FEATURE:
<223> OTHER INFORMATION: reverse primer, 1492r, for the amplification of
      16S rDNA from MJM5123 genomic DNA

<400> SEQUENCE: 2

ggttaccttg ttacgactt                                                   19
```

-continued

[Formula 2: H-16]

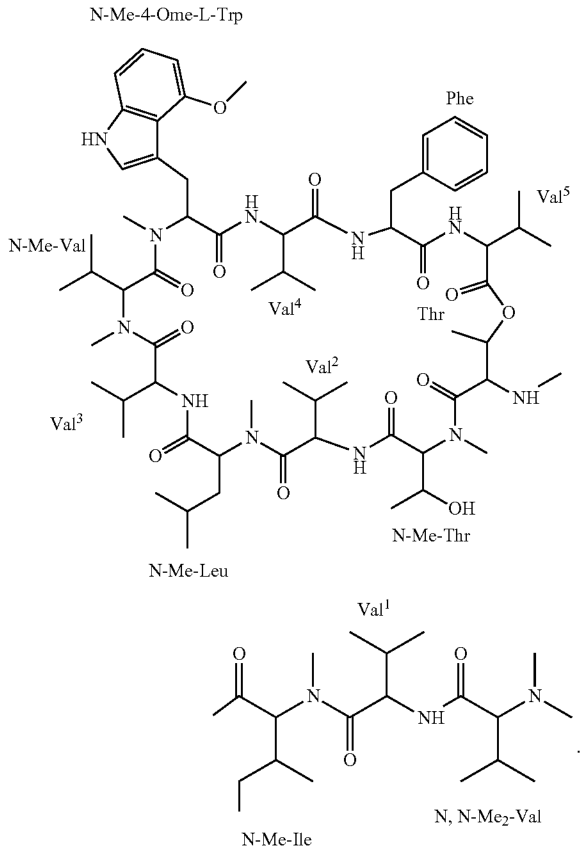

2. The pharmaceutical composition according to claim 1, wherein the *Mycobacterium* spp. related disease is tuberculosis.

3. A pharmaceutical composition according to claim 2, wherein the tuberculosis is MDR tuberculosis or XDR tuberculosis.

4. The pharmaceutical composition according to claim 1, wherein the composition further comprises one or more antimycobacterial agents.

5. The pharmaceutical composition according to claim 4 wherein the antimycobacterial agent is selected from the group consisting of isoniazid, rifampicin, ethambutol, pyrazinamide, streptomycin, amikacin, capreomycin, kanamycin, ciprofloxacin, ofloxacin, gatifloxacin, moxifloxacin; rifabutin, protionamide, ethionamide, cycloserine, linezolid, clofazimine, amoxicillin/clavulanate, clarithromycin, Bedaquiline, Dalamanid, Sutezolid, rifapentine and boron-containing LeuRS inhibitors.

6. The pharmaceutical composition according to claim 4, wherein the compound of formula 1 or 2 and the at least one further compound are adapted for simultaneous, sequential or separate administration.

7. A process for the manufacture of the anti-TB cyclic peptide of Formula 1 or Formula 2

[Formula 1: H-14]

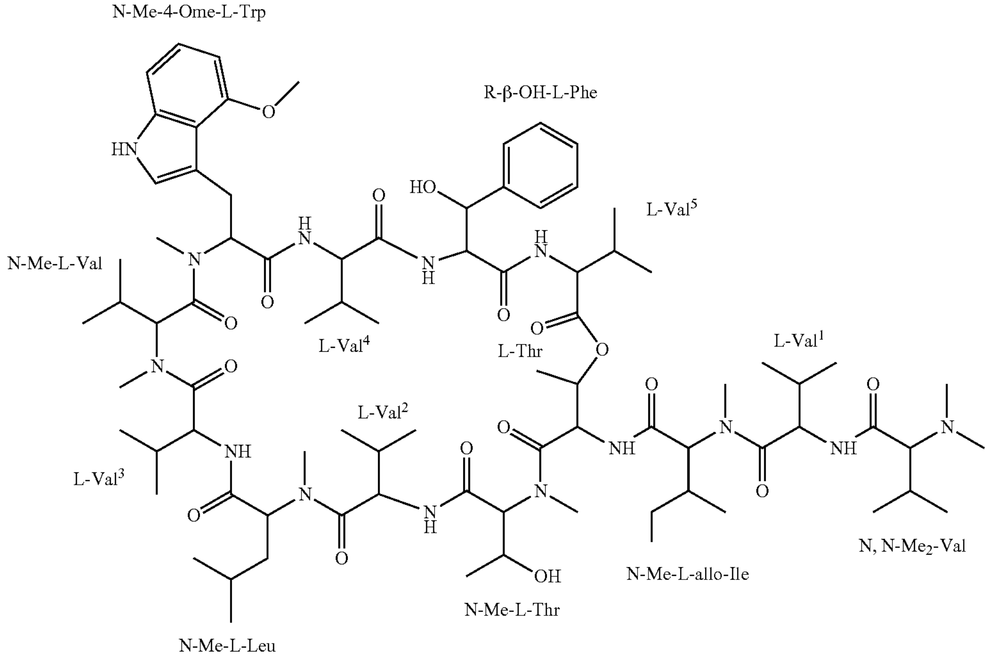

-continued

[Formula 2: H-16]

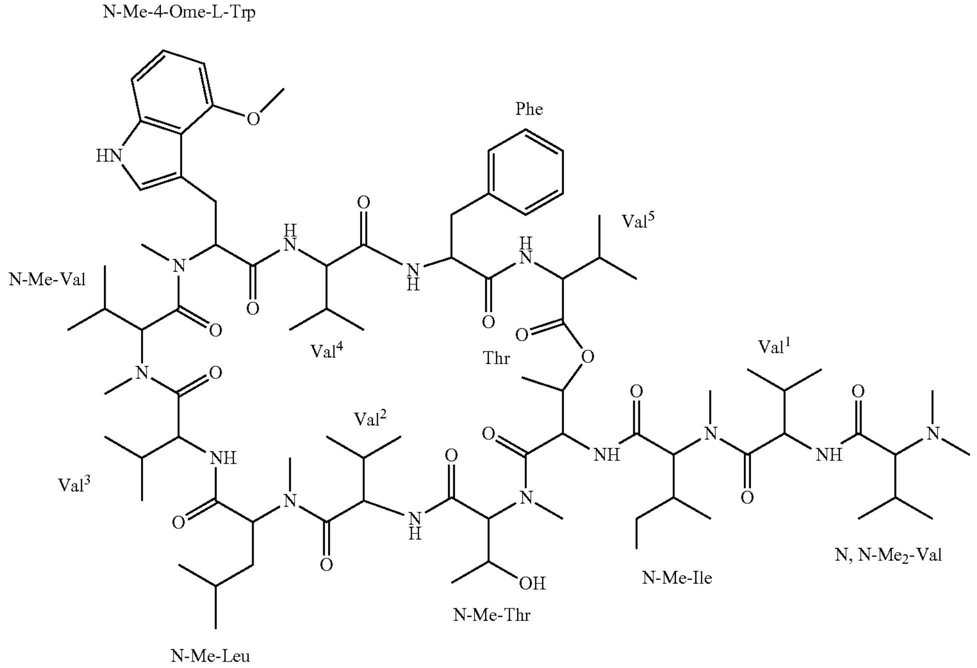

comprising; cultivating an antimycobacterial peptide-producing microorganism of the *Nonomuraea* sp. MJM5123 strain under aerobic conditions in an aqueous culture medium; and isolating anti-TB cyclic peptide by performing Vacuum liquid chromatography (VLC) of methanol extract of *Nonomuraea* sp. MJM5123 mycelia using methanol and chloroform as an eluent; performing Sephadex LH-20 open column chromatographyusing methanol as an eluent; and performing High Speed Countercurrent Chromatography (HSCCC) using HEMWat+2 as a solvent.

8. The process according to claim 7, wherein the step for isolating anti-Tuberculosis cyclic peptide comprises extracting *Nonomuraea* sp. MJM5123 mycelia using methanol as a solvent; adding water up to 30% of the methanol to make aqueous methanol; defatting the methanol extract using hexane; separating aqueous layer and adjusting to 65% aqueous methanol; extracting the aqueous layer using chloroform; concentrating and resolving the chloroform extract using methanol; performing Sephadex LH-20 column chromatography using methanol as an eluent; and performing HPLC equipped with column filled with reverse phase gel (RP-18).

9. The pharmaceutical composition according to claim 2, wherein the composition further comprises one or more antimycobacterial agents.

10. The pharmaceutical composition according to claim 3, wherein the composition further comprises one or more antimycobacterial agents.

11. The pharmaceutical composition according to claim 5, wherein the compound of formula 1 or 2 and the at least one further compound are adapted for simultaneous, sequential or separate administration.

* * * * *